(12) United States Patent
Makin, III et al.

(10) Patent No.: US 12,207,935 B2
(45) Date of Patent: Jan. 28, 2025

(54) QUANTITATIVE IMAGE-BASED DISORDER ANALYSIS FOR EARLY DETECTION OF MELANOMA TYPE FEATURES

(71) Applicant: THE BOARD OF TRUSTEES OF WESTERN MICHIGAN UNIVERSITY, Kalamazoo, MI (US)

(72) Inventors: Robert Allen Makin, III, Kalamazoo, MI (US); Steven Michael Durbin, Kalamazoo, MI (US)

(*) Notice: Subject to any disclaimer, the term of this patent is extended or adjusted under 35 U.S.C. 154(b) by 449 days.

(21) Appl. No.: 17/839,980

(22) Filed: Jun. 14, 2022

(65) Prior Publication Data

US 2023/0000426 A1    Jan. 5, 2023

Related U.S. Application Data

(60) Provisional application No. 63/217,840, filed on Jul. 2, 2021.

(51) Int. Cl.
   *A61B 5/00*    (2006.01)
   *G06T 7/00*    (2017.01)

(52) U.S. Cl.
   CPC ............ *A61B 5/444* (2013.01); *A61B 5/0059* (2013.01); *G06T 7/0012* (2013.01); *G06T 2207/30088* (2013.01)

(58) Field of Classification Search
   CPC ...... A61B 5/444; A61B 5/0059; G06T 7/0012
   See application file for complete search history.

(56) References Cited

U.S. PATENT DOCUMENTS

| | | | |
|---|---|---|---|
| 3,309,553 A | 3/1967 | Kroemer | |
| 3,413,533 A | 11/1968 | Kroemer et al. | |
| 4,792,832 A | 12/1988 | Baba et al. | |
| 4,833,101 A | 5/1989 | Fujii | |
| 4,978,853 A | 3/1990 | Hilal | |
| 6,081,612 A * | 6/2000 | Gutkowicz-Krusin | G06T 7/136 382/248 |
| 7,951,494 B2 | 5/2011 | Sawa et al. | |
| 8,981,382 B2 | 3/2015 | Gao | |
| 9,622,698 B2 | 4/2017 | Mestha et al. | |
| 9,864,903 B2 | 1/2018 | Cheswick | |

(Continued)

FOREIGN PATENT DOCUMENTS

| | | |
|---|---|---|
| CN | 111260645 A | 6/2020 |
| CN | 113435292 A | 9/2021 |

(Continued)

OTHER PUBLICATIONS

Morgan, RS., "Reciprocal ribose interactions: A possible structural motif in and between RNA's," Biosystems, vol. 5, 1973, pp. 95-97.

(Continued)

*Primary Examiner* — David Bilodeau

(57) ABSTRACT

A method of distinguishing benign and malignant skin conditions includes extracting a numerical value corresponding to an order parameter from an image of skin having a pigmented region. The numerical value of the order parameter may be utilized to assess the likelihood that a skin lesion is benign or malignant. The precise value may also be utilized to assess severity, which may include detecting changes in a skin lesion over time.

25 Claims, 10 Drawing Sheets
(7 of 10 Drawing Sheet(s) Filed in Color)

(56) References Cited

U.S. PATENT DOCUMENTS

| | | | |
|---|---|---|---|
| 9,876,248 B2 | 1/2018 | Hiraiwa et al. | |
| 10,381,673 B2 | 8/2019 | Miller et al. | |
| 10,446,189 B2 | 10/2019 | Zukerman et al. | |
| 10,810,725 B1 | 10/2020 | Dolhansky et al. | |
| 11,545,563 B2 | 1/2023 | Makin, III et al. | |
| 2003/0161513 A1* | 8/2003 | Drukker | G06T 7/0012 382/128 |
| 2005/0037406 A1* | 2/2005 | De La Torre-Bueno | G06T 5/50 435/6.12 |
| 2006/0269111 A1* | 11/2006 | Stoecker | G16H 30/40 382/128 |
| 2011/0046894 A1* | 2/2011 | Stamnes | A61B 5/7264 702/19 |
| 2012/0220474 A1* | 8/2012 | Kennedy | C12Q 1/6883 506/9 |
| 2013/0240026 A1 | 9/2013 | Atwater et al. | |
| 2014/0046197 A1* | 2/2014 | Lucassen | A61B 5/0075 600/477 |
| 2015/0213305 A1 | 7/2015 | Sundstrom | |
| 2016/0140405 A1 | 5/2016 | Graumann et al. | |
| 2017/0022571 A1* | 1/2017 | Malafa | C12Q 1/6886 |
| 2017/0172487 A1 | 6/2017 | Aharon | |
| 2017/0231550 A1* | 8/2017 | Do | G06T 7/0012 382/128 |
| 2017/0301086 A1* | 10/2017 | Jena | G06T 7/0012 |
| 2018/0083155 A1 | 3/2018 | Mahajan et al. | |
| 2018/0122969 A1 | 5/2018 | Olenick et al. | |
| 2018/0361287 A1 | 12/2018 | Zhang | |
| 2018/0365831 A1* | 12/2018 | Popp | G06T 7/0012 |
| 2019/0168144 A1 | 6/2019 | Umebayashi | |
| 2019/0336063 A1* | 11/2019 | Dascalu | A61B 5/0064 |
| 2020/0227751 A1 | 7/2020 | Mimura et al. | |
| 2020/0334347 A1 | 10/2020 | Hoyos et al. | |
| 2021/0036310 A1 | 2/2021 | Hou et al. | |
| 2021/0117690 A1 | 4/2021 | Ye | |
| 2021/0119237 A1 | 4/2021 | Lee et al. | |
| 2021/0202988 A1 | 7/2021 | Kim et al. | |
| 2021/0209754 A1* | 7/2021 | Mishra | G06T 7/90 |
| 2021/0349093 A1 | 11/2021 | Makin, III et al. | |
| 2021/0359324 A1 | 11/2021 | Armstrong | |
| 2022/0121884 A1 | 4/2022 | Zadeh et al. | |
| 2022/0347610 A1 | 11/2022 | Makin, III et al. | |
| 2022/0365243 A1 | 11/2022 | Makin, III et al. | |
| 2023/0000426 A1 | 1/2023 | Makin, III et al. | |

FOREIGN PATENT DOCUMENTS

| | | |
|---|---|---|
| EP | 3629232 A1 | 4/2020 |
| JP | 6191368 B2 | 9/2017 |
| WO | 2014072375 A1 | 5/2014 |
| WO | 2021137946 A1 | 7/2021 |
| WO | PCT/US23/24135 | 6/2023 |
| WO | PCT/US23/24243 | 6/2023 |

OTHER PUBLICATIONS

Laks, D.B., Wei, S.-H., and Zunger, A., "Evolution of alloy properties with long-range order," Phys. Rev. Lett., vol. 69, pp. 3766-3770 (1992).

Wei, S., Laks, D.B., and Zunger, A., "Dependence of the optical properties of semiconductor alloys on the degree of long-range order," Appl. Phys. Lett., vol. 62, pp. 1937-1939 (1993).

Ma, J., Deng, H.-X., Luo, J.-W., and Wei, S.-H., "Origin of the failed ensemble average rule for the band gaps of disordered nonisovalent semiconductor alloys," Phys. Rev. B 90, 115201 (2014).

Nakatsuka, S. and Nose, Y., "Order-Disorder Phenomena and Their Effects on Bandgap in ZnSnP2," J. Phys. Chem. C 121, 1040 (2017).

Ryan, M., Peterson, M.W., Williamson, D., Frey, J.S., Maciel, G.E., and Parkinson, B., "Metal site disorder in zinc tin phosphide," J. Mater. Res. 2, 528 (1987).

St-Jean, P., Seryogin, G., and Francoeur, S., "Band gap of sphalerite and chalcopyrite phases of epitaxial ZnSnP 2 ZnSnP2," Appl. Phys. Lett. 96, 231913 (2010).

Cowley, J.M., "X-Ray Measurement of Order in Single Crystals of Cu3Au," J. Appl. Phys., vol. 21, 24 (1950).

Feldberg, N., Aldous, J., Linhart, W., Phillips, L., Durose, K., Stampe, P., Kennedy, R., Scanlon, D., Vardar, G., Field, R., III et al., "Growth, disorder, and physical properties of ZnSnN2," Appl. Phys. Lett. 103, 042109 (2013) doi: 10.1063/1.4816438.

Keating, D. T. and Warren, B. E., "Long-Range Order in Beta-Brass and Cu3Au," J. Appl. Phys. 22, 286 (1951).

Senabulya, N., Feldberg, N., Makin, RA., Yang, Y., Shi, G., Jones, C.M., Kioupakis, E., Mathis, J., Clarke, R., and Durbin, S.M., "Stabilization of orthorhombic phase in single-crystal ZnSnN2 films," AIP Adv. 6, 075019 (2016) doi: 10.1063/1.4960109.

Achiele, K.P., "Paul Klee's 'Rhythmisches': A Recapitulation of the Bauhaus Years," Zeitschrift fur Kunstgeschichte 57, 75 (1994).

Anderson, C., Zucker, F., and Steitz, T., "Space-filling models of kinase clefts and conformation changes," Science 204, 375 (1979).

Bhuiyan, A.G., Sugita, K., Kasashima, K., Hashimoto, A., Yamamoto, A., and Davydov, V.Y., "Single-crystalline InN films with an absorption edge between 0.7 and 2 eV grown using different techniques and evidence of the actual band gap energy," Applied Physics Letters, 83, 4788 (2003).

Bleckley, S. and Schroeder, S.J., "Incorporating global features of rna motifs in predictions for an ensemble of secondary structures for encapsidated ms2 bacteriophage rna," RNA 18, 1309 (2012).

Burstein, E., "Anomalous Optical Absorption Limit in InSb," Phys. Rev. 93, 632 (1954).

Cho, S.-H., "Effects of growth temperature on the properties of ZnO thin films grown by radio-frequency magnetron , sputtering," Transactions on Electrical and Electronic Materials 10, 185 (2009).

Cray, C. and Rowley, G., "Chinese and Western Composition: A Conversation between an Artist and an Art Historian," College Art Journal 15, 6 (1955).

Dimroth et al., "Wafer Bonded Four-junction GaInP/GaAs//GaInAsP/GaInAs Concentrator Solar Cells with 44.7% Efficiency," Progress in Pholovoltaics: Research and Applications, Prog. Pholovolt: Res. Appl. 2014, vol. 22, published Jan. 13, 2014, pp. 277-282, https://doi.org/10.1002/pip.2475.

Dixon, J.R., and Bis, R.F., "Band Inversion and the Electrical Properties of PbxSn1—xTe," Phys. Rev. 176, 942 (1968).

Feldberg et al., "ZnSnN2: A New Earth-Abundant Element Semiconductor for Solar Cells," Department of Physics, University at Buffalo, The State University of New York, Buffalo, NY, USA, IEEE, 2011 978-1-4673-0066-7/12, pp. J02524-002527 (4 pages).

Haddad, D.B., Thakur, U.S., Naik, V.M., Aun ER, G.W., Naik, R., and Wenger, L.E., "Optical Band Gap Measurements of InN Films in the Strong Degeneracy Limit," MRS Proceedings 743, L 11.22 (2002).

Holonyak, N. and Bevacqua, S.F., "Coherent (Visible) Light Emission From Ga(As1xPx) Junctions," Applied Physics Letters 1, 82 (1962).

Ichimiya, A., Cohen, P.I., and Cohen, P.I., "Reflection high-energy electron diffraction," Cambridge University Dress (2004).

Inushima, T., Mamutin, V., Vekshin, V., Ivanov, S., Sakon, T., Motokawa, M., and Ohoya, S., "Physical properties of InN with the band gap energy of 1.1ev," Journal of Crystal Growth 227-228, 481 (2001).

Janssen, B., Burgoyne, J.A., and Honing, H., "Predicting Variation of Folk Songs: A Corpus Analysis Study on the Memorability of Melodies," Frontiers in Psychology 8, 621 (2017).

Ji, X.H., Lau, S.P., Yang, HY., and Zhang, Q.Y., "Thin Solid Films" 515, 4619 (2007).

Kronig, R.D.L., Penney, W.G., and Fowler, R.H., "Quantum mechanics of electrons in crystal lattices," Proceedings of the Royal Society of London, Series A, Containing Papers of a Mathematical and Physical Character 130,499 (1931).

Kurimoto, E., Hangyo, M., Harisma, H., Yoshimoto, M., Yamaguchi, T., Araki, T., Nanishi, Y., and Kisoda, K., "Spectroscopic observation of oxidation process in InN," Applied Physics Letters 84, 212 (2004).

(56) References Cited

OTHER PUBLICATIONS

Lacklison, D.E., Orton, J.W., Harrison, I., Cheng, T.S., Jenkins, L.C., Foxon, C.T., and Hooper, S.E., "Band gap of GaN films grown by molecular-beam epitaxy on GaAs and GaP subsrtates," Journal of Applied Physics 78, 1838 (1995).

Makin et al., "Order Parameter and Band Gap of ZnSnN2," Department of Electrical and Computer Engineering, Nestern Michigan University, Kalamazoo, Michigan, 978-1-5386-8529-7/18, 2018, IEEE, pp. 3865-3868.

Mang, A., Reimann, K., and Robenacke, S., "Band gaps, crystal-field splitting, spin-orbit coupling, and exciton binding energies in ZnO under hydrostatic pressure," Solid State Communications 94, 251 (1995).

Moss, T.S., "The interpretation of the properties of indium antimonide," Proceedings of the Physical Society, Section B 67, 775 (1954).

Ruhle, S., "Tabulated Values of the Shockley-Queisser Limit for Single Junction Solar Cells," Solar Energy Consulting, vol. 130, 2016, pp. 139-147, <http://dx.doi.org/10.1016/j.solener.2016.02.15>.

Slotboom, J., and De Graaff, H., "Measurements of bandgap narrowing in Si bipolar transistors," Solid-State Electronics 19, 857 (1976).

Walukiewicz, W., Li, S., Wu, J., Yu, K., Ager, J., Haller, E., Lu, H., and Schaff, W.J., "Optical properties and electronic structure of InN and In-rich group III-nitride alloys," Journal of Crystal Growth 269, 119 (2004).

Bragg, W. L. and Williams, E. J., "The effect of thermal agitation on atomic arrangement in alloys—III," Proceedings of the Royal Society of London, Series A, Mathematical and Physical Sciences, vol. 152, Oct. 15, 1935, pp. 231-252.

Ager, J.W., Walukiewicz, W., Shan, W., Yu, K.M., Li, S.X., Haller, E.E., Lu, H., and Schaff, W.J., "Multiphonon resonance Raman scattering in InxGa1—xN," Phys. Rev. B 72, 155204 (2005).

Arnaudov, B., Paskova, T., Paskov, P.P., Magnusson, B., Valcheva, E., Monemar, B., Lu, H., Schaff W.J., Amano, H., and Akasaki, I., "Energy position of near-band-edge emission spectra of InN epitaxial layers with different doping levels," Phys. Rev. B 69, 115216 (2004).

Berggren, K.F. and Sernelius, B.E., "Band-gap narrowing in heavily doped many-valley semiconductors," Phys. Rev. B 24, 1971 (1981).

Brodsky, M.H. and Title, R.S., "Electron Spin Resonance in Amorphous Silicon, Germanium, and Silicon Carbide," Phys. Rev. Lett. 23, 581 (1969).

Cuong, T.V., Pham, V.H., Tran, Q.T., Hahn, S.H., Chung, J.S., Shin, E.W., and Kim, E.J., "Photoluminescence and Raman studies of graphene thin films prepared by reduction of graphene oxide," Materials Letters 64, 399 (2010).

Davydov, V.Y., Klochikhin, A.A., Emtsev, V.V., Smirnov, A.N., Goncharuk, I.N., Sakharov, AV., Kurdyukov, D.A., Baidakova, M.V., Vekshin, V.A., Ivanov, S.V., Aderhold, J., Graul, J., Hashimoto, A., and Yamamoto, A., "Photoluminescence and Raman study of hexagonal InN and In-rich InGaN alloys," Physica Status Solidi (b) 240, 425 (2003).

D'Innocenzo, V., Srimath Kandada, A.R., De Bastiani, M., Gandini, M., and Petrozza, A., "Tuning the Light Emission Properties by Band Gap Engineering in Hybrid Lead Halide Perovskite," J. Am. Chem. Soc. 136, 17730 2014).

Dixit, V., Rodrigues, B., Bhat, H., Venkataraghavan, R., Chandrasekaran, K., and Arora, B., "Growth of InSb epitaxial layers on GaAs (001) substrates of LPE and their characterizations," Journal of Crystal Growth 235, 154 (2002).

Fogal, B., O'Leary, S., Lockwood, D., Baribeau, J.-M., Noel, M., and Zwinkels, J., "Disorder and the optical properties of amorphous silicon grown by molecular beam epitaxy," Solid State Communications 120, 429 2001).

Geim, A.K. and Novoselov, K.S., "The rise of graphene," Nature Matter 6, 183 (2007).

Guo, Q., Kusunoki, Y., Ding, Y., Tanaka, T., and Nishio, M., "Properties of InGaN Films Grown by Reactive Sputtering," Japanese Journal of Applied Physics 49, 081203 (2010).

Kalt, H. and Rinker, M., "Band-gap renormalization in semiconductors with multiple inequivalent valleys," Phys. Rev. B 45, 1139 (1992).

Kong, L., Liu, G., Gong, J., Hu, Q., Schaller, R.D., Dera, P., Zhang, D., Liu, Z., Yang, W., Zhu, K., Tang, Y., Wang, C., Wei, S.-H., Xu, T., and Mao, H.-K., "Simultaneous band-gap narrowing and carrier-lifetime prolongation of organic-inorganic trihalide perovskites," Proceedings of the National Academy of Sciences 113, 8910 (2016), https://www.pnas.org/content/113/32/8910.full.pdf.

Kohli, & Gupta, A. (2021). Detecting DeepFake, FaceSwap and Face2Face facial forgeries using frequency CNN. Multimedia Tools and Applications, 80(12), 18461-18478. https://doi.org/10.1007/s11042-020-10420-8.

Mazaheri, G., Roy-Chowdhury, A. K. (2022). Detection and localization of facial expression manipulations. 2022 IEEE/CVF Winter Conference on Applications of Computer Vision (WACV). https://doi.org/10.1109/https://doi.org/10.1109/wacv51458.2022.00283.

S. Agarwal, H. Farid, O. Fried and M. Agrawala, "Detecting Deep-Fake Videos from Phoneme-Viseme Mismatches," 2020 IEEE/CVF Conference on Computer Vision and Pattern Recognition Workshops (CVPRW), Seattle, WA, USA, 2020, pp. 2814-2822, doi: 10.1109/CVPRW50498.2020.00338.

Sun, Y., Zhang, Z., Qiu, C., Wang, L., Sun, L., Wang, Z. (2022). Faketransformer: Exposing face forgery from spatial-temporal representation modeled by facial pixel variations. 2022 7th International Conference on Intelligent Computing and Signal Processing (ICSP). https://doi.org/10.1109/icsp54964.2022.9778420.

Z. Zhang, C. Mal, B. Ding and M. Gao, "Detecting Manipulated Facial Videos: A Time Series Solution," 2020 25th International Conference on Pattern Recognition (ICPR), Milan, Italy, 2021, pp. 2817-2823, doi: 10.1109/ICPR48806.2021.9412610.

C. Ciszak et al., "Raman spectra analysis of ZrO2 thermally grown on Zircaloy substrates irradiated with heavy ion: Effects of oxygen isotopic substitution," Journal of Raman Spectroscopy, vol. 50, No. 3, pp. 425-435, 2019.

C. Zhang et al., "Ionic conductivity and its temperature dependence of atmospheric plasmasprayed yttria stabilized zirconia electrolyte," Materials Science and Engineering: B, vol. 137, No. 1, pp. 24-30, Feb. 2007.

Chen, X.J., et al. "Influence of microstructure on the ionic conductivity of yttria-stabilized zirconia electrolyte." Materials Science and Engineering A vol. 335 p. 246-252 [online]. Sep. 25, 2002 (Sep. 25, 2002) (retrieved on Aug. 2, 2023) Retrieved from the Internet: <URL: https://www.sciencedirect.com/science/article/abs/pii/S0921509301019359> <DOI: 10.1016/S0921-5093(01 )01935-9>.

D. Chen, S. Su, Z. Yu and L. Lu, "Geometrical Optimization of the Composite Cathode in a Solid Oxide Fuel Cell," 2011 Asia-Pacific Power and Energy Engineering Conference, Wuhan, China, 2011, pp. 1-4, doi: 10.1109/APPEEC.2011.5748908.

F. T. Ciacchi, K. M. Crane, and S. P. S. Badwal, "Evaluation of commercial zirconia powders forsolid oxide fuel cells," Solid State Ionics, vol. 73, No. 1, pp. 49-61, Oct. 1994.

Feng, X., Chien, P.-H., Wang, Y., Patel, S., Wang, P., Liu, H., Immediato-Scuotto, M., Hu, Y.-Y. (2020). Enhanced ion conduction by enforcing structural disorder in Li-deficient argyrodites li6-xps5-xcl1+x. Energy Storage Materials, 30, 67-73. https://doi.org/10.1016/j.ensm.2020.04.042.

Gamon, J., Dyer, M. S., Duff, B. B., Vasylenko, A., Daniels, L. M., Zanella, M., Gaultois, M. W., Blanc, F., Claridge, J. B., Rosseinsky, M. J. (2021). Li4.3als3.3cl0.7: A sulfide-chloride lithium ion conductor with highly disordered structure and increased conductivity. Chemistry of Materials, 33(22), 8733-8744. https://doi.org/10.1021/acs.chemmater.1c02751.

Garcia-Barriocanal, J., Rivera-Calzada, A., Varela, M., Sefrioui, Z., Diaz-Guillen, M.R., Moreno, K.J., Díaz-Guillén, J. A., Iborra, E., Fuentes, A.F., Pennycook, S.J., Leon, C. and Santamaria, J. (2009), Tailoring Disorder and Dimensionality: Strategies for Improved Solid Oxide Fuel Cell Electrolytes. ChemPhysChem, 10: 1003-1011. https://doi.org/10.1002/cphc.200800691.

Hattori et al., "Change in Conductivity of Yttria Stabilized Zirconia," Journal of the Japan Society of Powder and Powder Metallurgy, vol. 50, No. 4, pp. 297-301, 2003.

(56) References Cited

OTHER PUBLICATIONS

Hu, N., Khan, M., Wang, Y., Song, X., Lin, C., Chang, C., Zeng, Y. (2017). Effect of microstructure on the thermal conductivity of plasma sprayed Y2O3 stabilized zirconia (8% YSZ). Coatings, 7(11), 198. https://doi.org/10.3390/coatings7110198.

I. R. Gibson, G. P. Dransfield, and J. T. S. Irvine, "Sinterability of commercial 8 mol% yttriastabilized zirconia powders and the effect of sintered density on the ionic conductivity," Journal of Materials Science, vol. 33, No. 17, pp. 4297-4305, Sep. 1998.

ISR for PCT/US23/24243 dated Sep. 8, 2023.

O. H. Kwon et al., "Investigation of the electrical conductivity of sintered monoclinic zirconia (ZrO2)," Ceramics International, vol. 43, No. 11, pp. 8236-8245, Aug. 2017.

Tu, Z., Tian, Y., Liu, M., Jin, B., Akbar, M., Mushtaq, N., Wang, X., Dong, W., Wang, B., Xia, C. (2021). Remarkable ionic conductivity in a LZO-SDC composite for low-temperature solid oxide fuel cells. Nanomaterials, 11 (9), 2277. https://doi.org/10.3390/nano11092277.

Wohlmuth, D., Epp, V., Bottke, P., Hanzu, I., Bitschnau, B., Letofsky-Papst, I., Kriechbaum, M., Amenitsch, H., Hofer, F., Wilkening, M. (2014). Order vs. disorder—a huge increase in ionic conductivity of nanocrystalline LiAlO_2 embedded in an amorphous-like matrix of lithium aluminate. J. Mater. Chem. A, 2(47), 20295-20306. https://doi.org/10.1039/c4ta02923b.

Y.-Z. Xing, C.-J. Li, Q. Zhang, C.-X. Li, and G.-J. Yang, "Influence of Microstructure on the Ionic Conductivity of Plasma-Sprayed Yttria-Stabilized Zirconia Deposits," Journal of the American Ceramic Society, vol. 91, No. 12, pp. 3931-3936, 2008.

Aaziri, K., Kycia, S., Roorda, S., Chicoine, M., Robertson, J.L., Wang, J., and Moss, S.C., "High Resolution Radial Distribution Function of Pure Amorphous Silicon," Phys. Rev. Lett. 82, 3460 (1999).

Lockwood, D.J. and Wang, A.G., "Quantum confinement induced photoluminescence in porous silicon," Solid State Communications 94, 905 (1995).

Makin, Robert A., Quantification and Influence of Cation Sublattice Disorder in Ternary Materials With Specific Application to SnSnN2, Western Michigan University, 2019.

Manser, J.S. and Kamat, P.V., "Band filling with free charge carriers in organometal halide perovskites," Nature Photonics 8, 737 (2014).

Meher, S.R., Biju, K.P., and Jain, M.K., "Raman spectroscopic investigation of phase separation and compositional fluctuations in nanocrystalline InGa1xN thin films prepared by modified activated reactive evaporation," Physica Status Solidi (a) 208, 2655 (2011).

Perez, J.M., Villalobos, J., McNeill, P., Prasad, J., Cheek, R., Kelber, J., Estrera, J.P., Stevens, P. D., and Glosser, R., "Direct evidence for the amorphous silicon phase in visible photoluminescent porous silicon," Applied Physics Letters 61,563 (1992).

Potts, R.B., "Some generalized order-disorder transformations," Mathematical Proceedings of the Cambridge Philosophical Society 48, 106 (1952).

Prokes, S.M. and Glembocki, O.J., "Role of interfacial oxide-related defects in the red-light emission in porous silicon," Phys. Rev. B 49, 2238 (1994).

Robins, L., Paul, A., Parker, C., Roberts, J., Bedair, S., Piner., E., and El-Masry, N., "Optical Absorption Raman, and Photoluminescence Excitation Spectroscopy of Inhomogeneous InGaN Films," MRS Proceedings 537, 33.22 (1998).

Senthilkumar, V., Venkatachalam, S., Viswanathan, C., Gopal, S., Narayandass, S.K., Mangalaraj, D., Wilson, K.C., and Vijayakumar, K.P., "Influence of substrate temperature on the properties of ,vacuum evaporated InSb films," Crystal Research and Technology 40, 573 (2005).

Sokolov, A.P., Shebanin, A.P., Golikova, O.A., and Mezdrogina, M.M., "Structural disorder and optical gap fluctuations in amorphous silicon," Journal of Physics: Condensed Matter 3, 9887 (1991).

Sood, A.K., Jayaram, K., and Muthu, D.V.S., "Raman and high-pressure photoluminescence studies on porous silicon," Journal of Applied Physics 72, 4963 (1992).

Tanino, H., Kuprin, A., Deai, H., and Koshida, N., "Raman study of free-standing porous silicon," Phys. Rev. B 63, 1937 (1996).

Tsu, R., Shen, H., and Dutta, M., "Correlation of Raman and photoluminescence spectra of porous silicon," Applied Physics Letters 60, 112 (1992).

Ising E:, "Beitrag zur Theorie des Ferromagnetismus," Zeitschrift fOr Physik 32 (1924), 6 pages.

Warren, 8., "X-Ray Diffraction," Dover Books on Physics (Dover, New York, 2012), 74 pages.

European Commission, DG Enterprise and Industry, "Critical raw materials for the EU Report of the Ad-hoc Working Group on defining critical raw materials", European Commission, Jul. 30, 2010, 84 pages.

Fateley et al., "Practical Methods for Selection Rules" (pp. 1-42 of this book originally appeared as "Infrared and Raman Selection Rules for Molecular and Lattice Vibrations: The Correlation Method," Wiley-Interscience, New York (1972), 33 pages.

Ichimiya, A. and Cohen, P., "Kinematic Electron Diffraction," Cambridge University Press, Cambridge, England, 2004, 23 pages.

Ising et al., "The Fate of Ernst Ising and the Fate of his Model," Jun. 6, 2017, 46 pages.

Kochmanski, Martin S. Note on the E. Ising's Paper, Bitrag Zur Theorie Des Ferromagnetismus, Feb. 13, 2008, 4 pages.

Makin et al., "Supplementary Information for Alloy-Free Band Gap Tuning Across the Visible Spectrum," at least as early as Jun. 27, 2019, 6 pages.

Wikipedia, "Ising model," Last edited on Apr. 4, 2022, 29 pages.

Boigard, H., Alimova, A., Martin, G.R, Katz, A., Gottlieb, P., Galarza, J.M., "Zika virus-like particle (VLP) based vaccine," PLOS Negl. Trop. Dis., May 2017, 11(5):e0005608.

Bonnez, W. et al., "Isolation and propagation of human papillomavirus type 16 in human xenografts implanted in the severe combined immunodeficiency mouse," J_ Virol., 72, pp. 5256-5261, 1998.

Carter, C.B. and Williams, D.B. (Eds.), "Transmission Electron Microscopy: Diffraction, Imaging, and Spectrometry," Springer International Publishing, 2016, Available from: https://www_springer.com/gp/book/9783319266497.

CDC, "H1N1 Flu," Images of the H1N1 Influenza Virus, at least as early as May 6, 2019, Available from: https://www.cdc.gov/h1n1flu/images_htm?s_cid=cs_001.

Chan, W., Zhou, H., Kemble, G., Jin, H., "The cold adapted and temperature sensitive influenza A/Ann Arbor/6/60 virus, the master donor virus for live attenuated influenza vaccines, has multiple defects in replication at the restrictive temperature," Virology, Oct. 25, 2008, vol. 380(2), pp. 304-311.

Chua, K., Mee Hoo Wong, E., Cropp, B., Hyatt, A., "Role of electron microscopy in Nipah virus outbreak investigation iind control," The Medical Journal of Malaysia, Jun. 2, 2007, vol. 62, pp. 139-142.

Cohen, K. W. and Frahm, N., "Current views on the potential for development of a HIV vaccine," Expert Opinion Biological Therapy, 17:3, pp. 295-303, 2017.

Cullity, B.D., "Elements of x-ray diffraction," Addison-Wesley Publishing Company, Inc., 1978.

Cunha, A.J.L.A. da, de Magalhaes-Barbosa, M.C., Lima-Setta, F., Medronho, R. de A., Prata-Barbosa, A., "Microcephaly Case Fatality Rate Associated with Zika Virus Infection in Brazil: Current Estimates," Pediatr. Infect. Dis. U., 2017, vol. 36(5), pp. 528-530.

Eckert, A., Higgins, D., MAMS, CDC, "Illustration of a Coronavirus," Public Health Image Library, 2020, Available from: https://phil.cdc.gov/details .aspx?pid=23312.

Fibriansah, G., Ng, T-S., Kostyuchenko, V.A., Lee, J., Lee, S., Wang, J. et al., "Structural Changes in Dengue Virus When Exposed to a Temperature of 37° C.," Journal of Virology, Jul. 2013, vol. 87(13), pp. 7585-7592.

Gels, T., Schagger, H. and von Jagow, G., "Tricine-sodium dodecyl sulfate-polyacrylamide gel electrophoresis for the separation of proteins in the range from 1 to 100 kDa," Anal. Biochem., vol. 166, pp. 368-379, 1987.

Hierholzer, J.C. and Kabara, J. J., "In Vitro Effects of Monolaurin Compounds on Enveloped RNA and DNA Viruses," Journal of Food Safety, vol. 4, pp. 1-12, 1982.

(56) References Cited

OTHER PUBLICATIONS

Hyatt, A.D., Zaki, S.R., Goldsmith, C.S., Wise, T.G., Hengstberger, S.G., "Ultrastructure of Hendra virus and Nipah virus within cultured cells and host animals," Microbes and Infection, Apr. 2001, 1 ;3(4), pp. 297-306.

Jordan, D., CDC, "3D rendering of a whole influenza (flu) virus," Public Health Image Library, 2019, Available from: https://phil.cdc.gov/Details.aspx?pid=23227.

Kenmoe, S., Demanou, M., Bigna, J.J., Nde Kengne, C., Fatawou Modiyinji, A., Simo, F.B.N. et al., "Case fatality rate and risk factors for Nipah virus encephalitis: A systematic review and meta-analysis," J. Clin. Virol., 2019, vol. 117, pp. 19-26.

Landau, L.D., "On the Theory of Phase Transitions," Zh. Esksp. Teor. Fiz. 7, pp. 19-32, 1937.

Monaghan, P., Green, D., Pallister, J., Klein, R., White, J., Williams, C. et al., "Detailed morphological characterisation of Hendra virus infection of different cell types using super-resolution and conventional imaging," Virology Journal, Nov. 27, 2014, 11:200, pp. 1-12.

Monath, T.P., "Treatment of yellow fever," Antiviral Research, vol. 78, pp. 116-124, 2008.

National Center for Emerging and Zoonotic Infectious Diseases, "Hendra Virus Disease (HeV)," Feb. 2021, Available from: https://www.cdc.gov/vhf/hendra/pdf/factsheet.pdf.

NIAID, "1918 H1N1 Virus Particles," 2018, Available from: https://www.flickr.com/photos/niaid/30012820867/.

NIAID, "Zika Virus," 2016, Available from: https://www.flickr.com/photos/niaid/27023892862/.

Nickol, M.E. and Kindrachuk, J., "A year of terror and a century of reflection: perspectives on the great influenza pandemic of 1918-1919," BMC Infectious Diseases, Feb. 6, 2019, vol. 19:117, 10 pages.

Pankrac, J., Klein, K., McKay, P.F., King, D.F.L., Bain, K., Knapp, J. et al., "A heterogeneous human immunodeficiency virus-like particle (VLP) formulation produced by a novel vector system," NPJ Vaccines, Jan. 19, 2018, 3(1), pp. 1-10.

Rerks-Ngarm, S., Pitisuttithum, P., Nitayaphan, S., Kaewkungwal, J., Chiu, J., Paris, R. et al., "Vaccination with ALVAC and AIDSVAX to prevent HIV-1 infection in Thailand," The New England Journal of Medicine, Dec. 3, 2009, vol. 361 (23), pp. 2209-2220.

Salinas, J.D. and Steiner, M.L., "West Nile Virus: Practice Essentials," Pathophysiology, Epidemiology, Medscape, Apr. 23, 2020 [cited May 5, 2020], Available from: https://emedicine.medscape.com/article/312210-overview.

Schiller, J. and Chackerian, B., "Why HIV Virions Have Low Numbers of Envelope Spikes: Implications for Vaccine Development," PLOS Pathog [Internet), Aug. 7, 2014 [cited May 5, 2020), vol. 10(8), Available from: https://www.ncbi.nlm.nih.gov/pmc/articles/PMC4125284/.

Kawamura, F., Yamada, N., Imai, M., and Taniguchi, T., "Synthesis of ZnSnN2 crystals via a high-pressure metathesis reaction," Cryst. Res_ & Technol., vol. 51,220 (2016).

Kresse, G, and Furthmuller, J., "Efficiency of ab-initio total energy calculations for metals and semiconductors using a plane-wave basis set," Comput. Mater. Sci. 6, 15 (1996).

Kresse, G. and Furthmuller, J., "Efficient iterative schemes for ab initio total-energy calculations using a plane-wave basis set," Phys. Rev. B 54, 11169 (1996).

Kresse, G. and Hafner, J., "Ab initio molecular dynamics for liquid metals," Phys. Rev. B 47, 558 (1993).

Kresse, G. and Hafner, J., "Ab initio molecular-dynamics simulation of the liquid-metal-amorphous-semiconductor transition in germanium," Phys. Rev. B 49, 14251 (1994).

Kresse, G. and Joubert, D., "From ultrasoft pseudopotentials to the projector augmented-wave method," Phys. Rev. B. f.101_ 59, 1758-1775 (1999).

Lahourcade, L., Coronel, N.C., Delaney, K.I., Shukla, S.K, Spaldin, N.A., and Atwater, H.A., "Structural and Optoelectronic Characterization of RF sputtered ZnSnN(2)," Advanced Materials, 25, 2562 (2013).

Lebens-Higgins, Z., Scanlon, D.O., Paik, H., Sallis, S., Nie, Y., Uchida, M., Quackenbush, N.F., Wahila, M.J., Sterbinsky, G.E., Arena, D.A., Woicik, J.C., Schlom, D.G., and Piper, L.F.J., "Direct Observation of Eletrostatically Driven Band Gap Renormalization in a Degenerate Perovskite Transparent Conducting Oxide," Phys. Rev. Lett. 116, 024602 (2016).

Lin, Yu-Jen et al., "A Rapid and Sensitive Early Diagnosis of Influenza Virus Subtype via Surface Enhanced Raman Scattering," Journal of Biosensors & Bioelectronics [Internet], 2014 [cited May 5, 2020], vol. 05(02), Available from: https://www.omicsonline.org/open-access/a-rapid-and-sensitive-early-diagnosis-of-influenza-virus-subtype-via-surface-enhanced-raman-scattering-2155-6210.1000150.php?aid=27090.

Liu, H., Li, Z., Cao, Y., Cui, Y., Yang, X., Meng Z. et al., "Effect of chondrocyte mitochondrial dysfunction on cartilage degeneration: A possible pathway for osteoarthritis pathology at the subcellular level," Molecular Medicine Reports, bet. 1, 2019, vol. 20(4), pp. 3308-3316.

Makin, R. A., Senabulya, N., Mathis, J., Feldberg, N., Miska, P., Clarke, R., and Durbin, S. M., "Growth of Ordered and Disordered ZnSnN2," J. Vac. Sci. Technol. B 35, 02B116 (2017).

Momma, K. and Izumi, F., "VESTA 3 for three-dimensional visualization of crystal, volumetric and morphology data," J. Appl. Crystallogr. 44, 1272 (2011).

NIAID, "MERS-CoV Particles," 2013, Available from: https://www.flickr.com/photos/niaid/8618697423/.

NIAID, "Novel Coronavirus SARS-CoV-2, 2020," Available from: https://www.flickr.com/photos/niaid/49641177636/.

Nussbaum-Krammer, C.I., Park, K-W, Li, L., Melki, R., Morimoto, RI., "Spreading of a Prion Domain from Cell-to-Cell Dy Vesicular Transport in Caenorhabditis elegans," PLOS Genetics, Mar. 28, 2013, vol. 9(3), e1003351.

Ober, J.A., "Mineral Commodity Summaries 2016," technical report, Reston, VA (2016).

Perdew, J.S., Burke, K., and Emzerhof, M., "Generalized Gradient Approximation Made Simple," Phys. Rev. Lett., vol. 77, pp. 3865-3868 (1996).

Peshek, T. J., Paudel, T. R., Kash, K., and Lambrecht, W.R.L., "Vibrational modes in ZnGeN2: Raman study and Theory," Phys. Rev. B 77, 235213 (2008).

Qin, R., Cao, H., Liang, L., Xie, Y., Zhuge, F., Zhang, H., Gao, J. Javaid, K., Liu, C., and Sun, W., "Semiconducting ZnSnN2 thin films for Si/ZnSnN2 p-n junctions," Appl. Phys, Lett., col. 108, 142104 (2016).

Quayle, P.T., Junno, G.T., He, K., Blanton, E.W., Shan, J., and Kash, K., "Vapor-liquid-solid synthesis of ZnSnN2," Phys. Status Solidi B, vol. 254, 1600718 (2017).

R. Jaffe, J. Price, M. Hitzman, and F. Slakey, "The Back Page, Energy Critical Elements," APS News, vol. 20, No. 4 (2011).

Reid, A.H., Taubenberger, J.K., Fanning, T.G., "The 1918 Spanish influenza: integrating history and biology," Microbes Infection, Jan. 2001, vol. 3(1), pp. 81-87.

Sarma, D.D., Shanthi, N., Barman, S.R., Hamada, N., Sawada, H., and Terakura, K., "Band Theory for Ground-State Properties and Exication Spectra of Perovskite LaMO3 ( M=Mn, Fe, Co, Ni)," Phys. Rev. Lett. 75, 1126 (1995).

Science Source, "SARS Coronavirus," TEM, at least as early as May 6, 2019, Available from: https://www.sciencesource.com/CS.aspx?VP3=SearchResult&ITEMID=SS2760539&POPUPPN= 1 &PopupIID=2OPEBMGD5GLU.

Sebastian, M., Peters, J.A., Stoumpos, C.C., Im, J., Kostina, S.S., Liu, S., Kanatzidis, M.G., Freeman, A.J. and Wessels, B.B., "Exitonic emissions and above-band-gap luminescence in the single-crystal perovskite Semiconductors CsPbBr3 and CsPbCl3m," Phys. Rev. B 92, 235210 (2015).

Shen, T.Y., Mitra, S.S., Prask, H. and Trevino, S.F., "Order-disorder phenomenon in sodium nitrate studied by low-frequency Raman scattering," Phys. Rev. B 12, 4530 (1975).

Upton, M.H., Choi, Y., Park, H., Liu, J., Meyers, D., Chakhalian, J., Middey, S., Kim, J.-W., and Ryan, "Novel Electronic Behavior Driving NdNiO3 Metal-Insulator Transition," P.J., Phys. Rev. Lett, 115, 036401 (2015).

(56) References Cited

OTHER PUBLICATIONS

Vidal, J., Trani, F., Bruneval, F., Marques, M.A.L., and Botti, S., "Effects of Electronic and Lattice Polarization on the Band Structure of Delafossite Transparent Conductive Oxides," Phys, Rev. Lett. 104, 136401 (2010).
Wei, S.-H., Ferreira, L.B., and Zunger, A., "First-principles calculation of the order-disorder transition in chalcopyrite semiconductors," Phys. Rev. B, vol. 45, pp. 2533-2536 (1992).
Wilchinsky, Z. W., "X-Ray Measurement of Order in the Alloy Cu3Au," J. Appl. Phys. 15, 806 (1944).
Yan, X.-W., Gao, M., Lu, Z.-Y., and Xiang, T., "Electronic Structures and Magnetic Order of Ordered-Fe-Vacancy Ternary Iron Selenides TIFe1.5Se2 and AFe1.5Se2 (A=K, Rb, or Cs)," Phys. Rev, Lett, 106, 087005 (2011).
Agranovski, I. E. et al., "Enhancement of the performance of low-efficiency HVAC filters due to continuous unipolar ion emission," Aerosol Science and Technology 40, 2006, pp. 963-968.
Auriemma, F. et al., "Structural Disorder in the α Form of Isotactic Polypropylene," Macromolecules 33, 8764 Oct. 1, 2000.
De Rosa, C. et al., "Polymorphism in polymers: A tool to tailor material's properties," Polymer Crystallization, 2020, 3: e10101.
G. Allegra, P. Corrandini and P. Ganis, "A model of the chain conformation of an isotactic vinyl polymer having opitcally active side groups," Macromolecular Chemistry and Physics, vol. 90, 1966, pp. 60-65.
H. Li, W. Wu, M.M. Bubakir, H. Chen, X. Zhong, Z. Liu, Y. Ding, and W. Yang, J., "Polypropylene fibers fabricated via a needleless melt-electrospinning device for marine oil-spill cleanup," Appl. Polymer Science, vol. 131, 2014.
Hiejima, Y. et al., "Investigation of the Molecular Mechanisms of Melting and Crystallization of Isotactic Polypropylene by in Situ Raman Spectroscopy," Macromolecules, vol. 50, 2017, pp. 5867-5876.
Hikosaka, M. et al., "The order of the molecular chains in isotactic polypropylene crystals," Polymer Journal, vol. 5, 1973, pp. 111-127.
Ho, R.-M. et al., "Helical architectures from self-assembly of chiral polymers and block copolymers," Progress in Polymer Science, vol. 36, 2011, pp. 376-453.
Lee, S. et al., "Reusable Polybenzimidazole Nanofiber Membrane Filter for Highly Breathable PM2.5 Dust Proof Mask", ACS Applied Materials & Interfaces 11, Jan. 7, 2019, pp. 2750-2757.
Liu, J. et al., "Low resistance bicomponent spunbond materials for fresh air filtration with ultra-high dust holding capacity," RSC Advances 7, 2017, pp. 43879-43887.
Principles of Equilibrium Statistical Mechanics, John Wiley & Sons, Ltd., 2005, Chapter 12—Mean-Field Theory III: Landau Formulation, pp. 432-469.
R. Ishidate, A. J. Markvoort, K. Maeda, and E. Yashima, "Unexpectedly Strong Chiral Amplification of Chiral/Achiral and Chiral/Chiral Copolymers of Biphenylylacetylenes and Further Enhancement/Inversion and Memory of the Macromolecular Helicity," J. Am. Chem. Soc. 141, 2019, pp. 7605-7614.
T.M. Birshtein and P.M. Luisi, "Conformation of optically active isotactic macromolecules," Vysokomol. Soedin. Polymer Science, vol. 6, 1238 (1964).
Calvo, F. et al., "Non-magnetic photospheric bright points in 3D simulations of the solar atmosphere," Astronomy & Astrophysics, vol. 596, id A43, Nov. 2016, 10 pages.
Zhao, Junwei et al., "Tracing p-Mode Waves From the Photosphere to the Corona in Active Regions," The Astrophysical Journal Letters, 830:L 17, Oct. 10, 2016, 7 pages.
A. Rössler, D. Cozzolino, L. Verdoliva, C. Riess, J. Thies, and M. Nießner, "FaceForensics++: Learning to Detect Manipulated Facial Images," 2019.
D. M. Montserrat et al., "Deepfakes Detection with Automatic Face Weighting," 2020 IEEE/CVF Conference on Computer Vision and Pattern Recognition Workshops (CVPRW), Seattle, WA, USA, 2020, pp. 2851-2859, doi: 10.1109/CVPRW50498.2020.00342.
ISR for PCT/US23/24135 dated Sep. 7, 2023.

K. Taya, N. Kuroki, N. Takeda, T. Hirose and M. Numa, "Detecting tampered regions in JPEG images via CNN," 2020 18th IEEE International New Circuits and Systems Conference (NEWCAS), Montreal, QC, Canada, 2020, pp. 202-205, doi: 10.1109/NEWCAS49341.2020.9159761.
Bragg, W.L. et al., "The effect of thermal agitation on atomic arrangement in alloys," Proceedings of the Royal Society of London. Series A, Containing Papers of a Mathematical and Physical Character 145, 699 (1934), 32 pages.
Bragg, W.L. et al., "The effect of thermal agitation on atomic arrangement in alloys II," Proceedings of the Royal Society of London, Series A—Mathematical and Physical Sciences 151, 540 (1935), 27 pages.
Makin, R.A. et al., "Alloy-Free Band Gap Tuning across the Visible Spectrum," Phys. Rev. Lett. 122, 256403 (Jun. 2019), 6 pages.
Makin, R.A. et al., "Revisiting semiconductor band gaps through structural motifs: An Ising model perspective," Phys. Rev. B 102, 115202 Sep. 8, 2020, 10 pages.
Makin, R. et al., "Quantitative disorder analysis and particle removal efficiency of polypropylene-based masks," MRS Advances, 1-9 (2020), 9 pages.
Makin, R.A. et al., "Structural Motifs, Disorder, and the Efficiency of Viral Vaccines," bioRxiv 10.1101/2020.06.08.139907 (2020), 21 pages.
Ziethlow, V. et al., "Assessment by electron-microscopy of recombinant Vibrio cholerae and *Salmonella* vaccine strains expressing enterotoxigenic *Escherichia coli*-specific surface antigens," Clinical Microbiology and Infection 14, 282 (2008), 5 pages.
Zhao, Q. et al., "Characterization of virus-like particles in Gardasil® by cryo transmission electron microscopy," Human Vaccines & Immunotherapeutics, Mar. 2014, publisher: Taylor & Francis, 734-9 pages.
Zhang, H. et al., "Efficient Neural Network Robustness Certification with General Activation Functions," in Advances in Neural Information Processing Systems 31, edited by S. Bengio, H. Wallach, H. Larochelle, K. Grauman, N. Cesa-Bianchi, and R. Garnett (Curran Associates, Inc., 2018) pp. 4939-4948, 10 pages.
Updated Recommendations for the Use of Typhoid Vaccine Advisory Committee on Immunization Practices, United States, 2015, 6 pages.
Aghanim, N. et al., 2018 results—I. Overview and the cosmological legacy of Planck, Astronomy & Astrophysics 641, A1 (2020), publisher: EDP Sciences, 56 pages.
R. A. et al., The sixteenth data release of the sloan digital sky surveys: First release from the apogee-2 southern survey and full release of eboss spectra (2019), 22 pages.
Jarrett, T., "Large Scale Structure in the Local Universe," The 2MASS Galaxy Catalog, Publications of the Astronomical Society of Australia 21, 396 (2004), 6 pages.
Grundy, W.M. et al., "Surface compositions across Pluto and Charon," Science 351, 10.1126/science.aad9189 (2016), publisher: American Association for the Advancement of Science.
Ulrich, R.K., "The Five-Minute Oscillations on the Solar Surface," The Astrophysical Journal 162, 993 (1970).
Aghanim, N.; "Planck 2018 results—VI. Cosmological parameters," Astronomy & Astrophysics 641, A6 (2020), publisher: EDP Sciences.
Science Source, "H3N2, Hong Kong Flu Virus," TEM, at least as early as May 6, 2019, Available from: https://www.sciencesource.com/CS.aspx?VP3=SearchResult&ITEMID=SS2760545.
Science Source, "H5N1, Influenza A, Avian Flu Virus," TEM, at least as early as May 6, 2019, Available from: https://www.sciencesource.com/CS.aspx?VP3=SearchResult&VBID=20PESQLF1 KBWQ&SM LS= 1 &RW=1920&RH=966#/.
Science Source, "HIV-1, Human Immunodeficiency Virus," TEM, at least as early as May 6, 2019, Available from: https://www.sciencesource.com/archive/HIV-1--Human-Immunodeficiency-Virus-TEM-SS2760525.html.
Science Source, "West Nile Virus," TEM, at least as early as May 6, 2019, Available from: https://www.sciencesource.com/archive/West-Nile-Virus-TEM-SS28384 79.html.
Smith, G.E., Sun, X., Bai, Y., Liu, Y.V., Massare, M.J., Pearce, M.B. et al., "Neuraminidase-based recombinant virus-like particles pro-

(56) References Cited

OTHER PUBLICATIONS tect against lethal avian influenza A(H5N1) virus infection in ferrets," Virology, 2017, pp. 509:90-509:97.
Taubenberger, J.K. and Morens, D.M., "1918 Influenza: the Mother of All Pandemics," Emerging Infectious Diseases Journal—CDC, vol. 12, No. 1, Jan. 2006, pp. 15-22, Available from: https://wwwnc.cdc.gov/eid/article/12/1 /05-0979article.
TEM of HIV-antigen AIDS vaccine from yeast, Stock Image—G255/0040, Science Photo Library, at least as early as May 6, 2019, Available from: https://www.sciencephoto.com/media/211839/view/tem-of-hiv-antigen-aids-vaccine-from-yeast.
Thanh Hung, N. and Trong Lan, N., "Improvement of Case-Management—A Key Factor to Reduce Case-Fatality Rate of Dengue Haemorrhagic Fever in Southern Viet Nam," Dengue Bulletin, vol. 27, 2003 [cited May 5, 2020], pp. 144-148, Available from: https://apps.who.int/iris/handle/10665/163789.
WHO Department of Communicable Disease Surveillance and Response, "Consensus document on the epidemiology of severe acute respiratory syndrome (SARS)," WHO Dept of Communicable Disease Surveillance and Response, 2003, Available from: www.who.int/csr/sars/en/WHOconsensus.pdf.
WHO Director-General's opening remarks at the media briefing on COVID-19, Mar. 3, 2020, Available from: https://www.who.int/dg/speeches/detail/who-director-general-s-opening-remarks-at-the-media-briefing-on-covid-19.
WHO, "FAQs: H5N1 influenza," WHO, at least as early as May 6, 2019, Available from: https://www.who.int/influenza/human_animal_interface/avian_influenza/h5n1_research/faqs/en/.
WHO, "Middle East respiratory syndrome coronavirus (MERS-CoV)," WHO, Mar. 15, 2021, Available from: http://www.who.int/emergencies/mers-cov/en/.
Yellow Fever Virus, TEM—Stock Image—C036/7398, Science Photo Library, at least as early as May 6, 2019, Available from: https://www.sciencephoto.com/media/864658/view/yellow-fever-virus-tem.
Yu, I-M, Zhang, W., Holdaway, H.A., Li, L., Kostyuchenko, V.A., Chipman, P. R. et al., "Structure of the immature dengue virus at low pH primes proteolytic maturation," Science, Mar. 28, 2008, vol. 319(5871), pp. 1834-1837.
Zhang, X., Sheng, J., Plevka, P., Kuhn, R.J., Diamond, M.S., Rossmann, M.G., "Dengue structure differs at the temperatures of its human and mosquito hosts," Proc. Natl. Acad. Sci., Apr. 23, 2013, vol. 110(17), pp. 6795-6799.
Lany, S., Fioretti, A.N., Zawadzki, P.P., Schelhas, L.T., Toberer, E.S., Zakutayev, A., and Tamboli, A.C., "Monte Carlo simulations of disorder in ZnSnN2 and the effects on the electronic structure," Phys. Rev. Mater. 1 (2017).
Makin, Robert A. et al., "Quantitative Disorder Analysis of Physical Systems Across Length Scales," Western Michigan University, Kalamazoo, Michigan, Mar. 17, 2020.
Austin, I., Goodman, C., and Pengelly, A., "New Semiconductors with the Chalcopyrite Structure," J. Electrochem. Soc. 103, 609 (1956).
Chen, S., Narang, P., Atwater, H.A., and Wang, L., "Phase Stability and Defect Physics of a Ternary ZnSnN2 Semiconductor: First Principles Insights," Adv. Mater. 26, 311 (2014).
Du, K., Bekele, C., Hayman, C.C., Angus, J.C., Pirouz, P. and Kash, K., "Synthesis and characterization of ZnGeN2 grown from elemental Zn and Ge sources," J. Cryst. Growth 310, 1057 (2008).
Fioretti, A.N., Zakutayev, A., Moutinho, H., Melamed, C., Perkins, J.D., Norman, A.G., Al-Jassim, M., Toberer, E.S., iind Tamboli, A.G., "Combinatorial insights into doping control and transport properties of zinc tin nitride," J. Mater. Chem. C 3, 11017 (2015).
Goodman, C. and Douglas, R., "New semiconducting compounds of diamond type structure," Physica 20, 1107 (1954).
Goodman, C.H. L., "A New Group of Compounds with Diamond type (Chalcopyrite) Structure," Nature 179,828 (1957).
Heyd, J., Scuseria, G.E., and Emzerhof, M., "Hybrid functionals based on a screened Coulomb potential," J. Chem. Phys., vol. 118, pp. 8207-8215 (2003).
Iliopoulos, E., Adikimenakis, A., Dimakis, E., Tsagaraki, K., Konstantinidis, G., and Georgakilas, A., "Active nitrogen species dependence on radiofrequency plasma source operating parameters and their role in GaN growth," J. Cryst. Growth, 278, 426 (2005).
Jaffe, J. and Zunger, A., "Anion displacements and the band-gap anomaly in ternary ABC2 chalcopyrite semiconductors," Phys. Rev. B, vol. 27, pp. 5176-5179 (1983).
Koblmuller, G., Gallinat, C., and Speck, J., "Surface kinetics and thermal instability of N-face InN grown by plasma-assisted molecular beam epitaxy," J. Appl. Phys. 101, 083516 (2007).
Lambrecht, W.R., Alldredge, E., and Kim, K., "Structure and phonons of ZnGeN2," Phys. Rev. B 72, 155202 (2005).
Larson, W.L., Maruska, H.P., and Stevenson, DA, "Synthesis and Properties of ZnGeN2," J. Electrochem. Soc., vol. 121, 1673 (1974).
Martinez, A.M., Arriaga, L.G., Fernandez, A.M., and Cano, U., "Band edges determination of CuInS2 thin films prepared by electrodeposition," Mater. Chem. Phys., vol. 88, pp. 417 (2004).
Narang, P., Chen, S., Coronel, N.C., Gui, S., Yano, J., Wang, L., Lewis, N.S., and Atwater, H.A., "Bandgap Tunability in Zn(Sn,Ge)N2 Semiconductor Alloys," Adv. Mater. 26, 1235 (2014).
Paudel, T.R. and Lambrecht, W.R., "First-principles calculation of the zone center phonons in ZnSiN2: Comparison With infrared data," Phys. Rev. B 76, 115205 (2007).
Paudel, T.R. and Lambrecht, W.R., "First-principles calculations of elasticity, polarization-related properties, and nonlinear optical coefficients in Zn—IV—N2 compounds," Phys_ Rev. B, vol. 79, 245205 (2009).
Prabukanthan, P. and Dhanasekaran, R., "Growth of CuGaS2 Single Crystals by Chemical Vapor Transport and Characterization," Cryst. Growth Des. 7, 618 (2007).
Punya, A., Lambrecht, W.R., and van Schilfgaarde M., "Quasiparticle band structure of Zn—IV—N2 compounds," Phys. Rev. B 84, pp. 16520401-165204-10 (2011).
Qi, Y., Liu, Q., Tang, K., Liang, Z., Ren, Z., and Liu, X., "Synthesis and Characterization of Nanostructured Wurtzite CuInS2: A New Cation Disordered Polymorph of CuInS2," J. Phys. Chem. C 113, 3939 (2009).
Quayle, P.C., Blanton, E.W., Punya, A., Junno, G.T., He, K., Han, L., Zhao, H., Shan, J., Lambrecht, W.R.L., and Kash, K., "Charge-neutral disorder and polytypes in heterovalent wurtzite-based ternary semiconductors: The importance of the octet rule," Phys_ Rev. B 91, pp. 205207-01-20507-14 (2015).
Quayle, P.C., He, K., Shan, J. and Kash, K., "Synthesis, lattice structure, and band gap of ZnSnN2," MRS Commun. 3, 135 (2013).
Scanlon, O. and Walsh, A., "Bandgap engineering of ZnSnP2 for high-efficiency solar cells," Appl. Phys. Lett. 100, 251911 (2012).
Van de Walle, A., Tiwary, P., de Jong, M., Olmsted, D., Asta, M., Dick, A., Shin, D., Wang, Y., Chen, L.-Q., and Liu, Z.-K., "Efficient stochastic generation of special quasirandom structures," CALPHAD: Comput. Coupling Phase Diagrams Thermo-chem., vol. 42, pp. 13-18 (2013).
Veal, T.D., Feldberg, N., Quackenbush, N.F., Linhart, W.M., Scanlon, D.O., Piper, L.F., and Durbin, S.M., "Band Gap Dependence on Cation Disorder in ZnSnN2 Solar Absorber," Adv. Energy Mater. 5, 1501462 (2015).
Viennois, R., Taliercio, T., Potin, V., Errebbahi, A., Gil, B., Charar, S., Haidoux, A., and Tedenac, J.S., "Prospective investigations of orthorhombic ZnGeN2: synthesis, lattice dynamics and optical properties," Mater. Sci. Eng. B 82, 45 (2001).
Wang, T., Ni, C., and Janotti, A., "Band alignment and p-type doping of ZnSnN2," Phys. Rev. B 95, pp. 205205-1-205205-6 (2017).
Zunger, A., Wei, S.-H., Ferreira, L.G., and Bernard, J.E., "Special quasirandom structures," Phys. Rev. Lett. 65, 353 (1990).
Loveluck, J. and Sokoloff, J., "Theory of the optical properties of phonon systems with disordered force constants, with application to NH4CI," J. Phys. Chem. Solids 34,869 (1973).
Berger, R.F., Fennie, C.J., and Neaton, J.B., "Band Gap and Edge Engineering via Ferroic Distortion and Anisotropic Strain: The Case of SrTiO3," Phys. Rev. Lett. 107, 146804 (2011).
Fioretti, A.N., Stokes, A., Young, M.R., Gorman, B., Toberer, E.S., Tamboli, A.C., and Zakutayev, A., "Effects of Hydrogen on Accep-

(56) References Cited

OTHER PUBLICATIONS tor Activation in Ternary Nitride Semiconductors," Advanced Electronic Materials, vol. 3, 1600544 (2017).

Harding, C., Pompei, F., Bordonaro, S.F., McGillicuddy, D.C., Burmistrov, D., Sanchez, L.D., "The daily, weekly, and seasonal cycles of body temperature analyzed at large scale," Chronobiology International, Dec. 2, 2019, vol. 36(12), pp. 1646-1657.

Jaroenjittichai, A.P. and Lambrecht, W.R.L., "Electronic band structure of Mg—IV—N2 compounds in the quasiparticle-self-consistent GW approximation," Phys. Rev. B 94, 125201 (2016).

Kanchiang, K., Cheiwchanchamnangij, T., Laosiritawron, Y., Pramchu, S., and Jaroenjittichai, A.P., "Structural and electronic properites of MgGexSn(1-x)N2 semiconductors: The density functional theory investigation," Journal of Physics: Conference Series, 1144, 012149 (2018).

\* cited by examiner

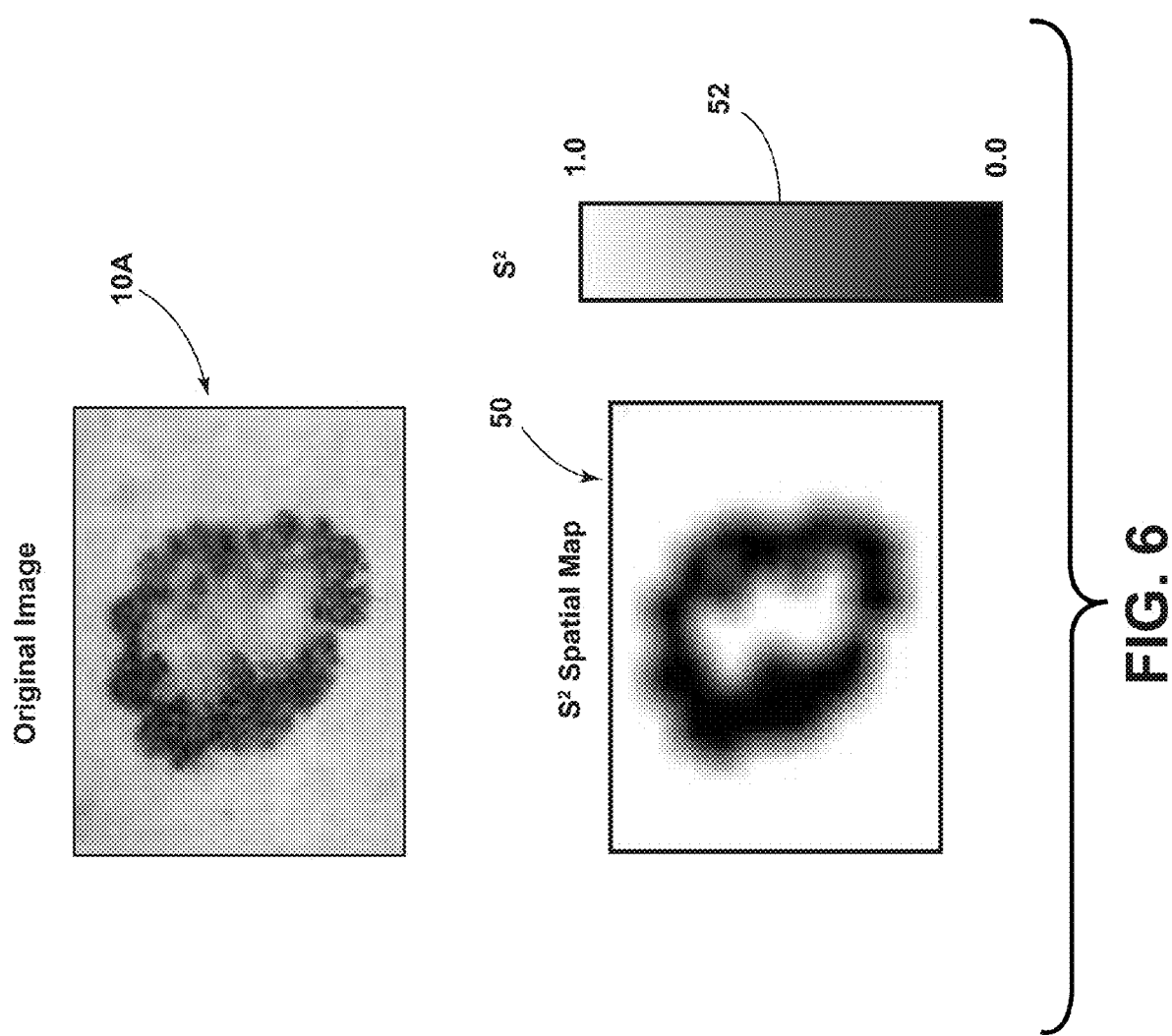

QUANTITATIVE IMAGE-BASED DISORDER ANALYSIS FOR EARLY DETECTION OF MELANOMA TYPE FEATURES

CROSS-REFERENCE TO RELATED APPLICATION

This application claims the benefit under 35 U.S.C. § 119(e) to U.S. Provisional Patent Application No. 63/217,840, filed Jul. 2, 2021, entitled "QUANTITATIVE IMAGE-BASED DISORDER ANALYSIS FOR EARLY DETECTION OF MELANOMA TYPE FEATURES," which is incorporated herein by reference in its entirety.

The present application is also related to U.S. patent application Ser. No. 17/735,729, filed May 3, 2022, entitled "ADVANCED WARNING FOR SOLAR FLARES FROM PHOTOSPHERE IMAGE ANALYSYS," and U.S. patent application Ser. No. 17/735,788, filed May 3, 2022, entitled "QUANTITATIVE DISORDER ANALYSIS AND PARTICLE REMOVAL EFFICIENCY OF FIBER-BASED FILTER MEDIA," the contents of each being incorporated herein by reference in their entirety.

STATEMENT REGARDING FEDERALLY SPONSORED RESEARCH OR DEVELOPMENT

This invention was made, in part, with government support under DMR-1410915 and DMR-2003581 awarded by the NSF. The government has certain rights in the invention.

BACKGROUND OF THE INVENTION

Skin lesions in humans may be caused by various conditions. Some pigmented skin conditions or lesions are benign, whereas other pigmented skin conditions or lesions are malignant.

Images of skin lesions may be used in an effort to identify the type of lesion, and to determine if a lesion is benign or malignant. For example, a specialist may be able to identify the type of a lesion by inspecting a dermatoscopic image.

BRIEF SUMMARY OF THE INVENTION

One aspect of the present disclosure is a method of distinguishing between benign and malignant conditions (e.g., skin lesions) utilizing a numerical value of an order parameter ($S^2$) that may be extracted from images of human skin. At least some aspects of the method may be implemented utilizing a computer and/or other suitable hardware and devices. In general, the order parameter has a range of 0 to 1, inclusive. According to an aspect of the present disclosure, an $S^2$ value below a predefined "malignant" value indicates that a region (e.g., a skin lesion) may be malignant, and an $S^2$ value above a predefined "benign" value indicates that a region (e.g., a skin lesion) may be benign. The method includes extracting (calculating) a numerical value of an order parameter ($S^2$) from an image such as a dermatoscopic image of skin, wherein the image includes at least one region (e.g., a pigmented skin lesion) having variable contrast. $S^2$ comprises a numerical value quantifying a degree of order present in the image. The numerical value of $S^2$ may be determined by dividing an area of the light regions by a total area that includes the light regions and the dark regions. The method may include comparing the numerical value of the extracted $S^2$ to a predefined maximum acceptable (malignant) $S^2$ value. It may be determined that the region (e.g., pigmented skin lesion) is likely to be malignant if the numerical value of the extracted $S^2$ is less than or equal to the predefined malignant $S^2$ value.

The method may optionally include determining that the pigmented skin lesion is likely to be benign if the numerical value of the extracted numerical value of $S^2$ is greater than or equal to a predefined benign $S^2$ value. Although the present disclosure is not limited to specific predefined values of $S^2$ indicating that a lesion is benign or malignant, benign lesions may typically have an $S^2$ value greater than 0.5, and malignant skin lesions may typically have an $S^2$ value that is less than 0.5. If the $S^2$ value of a lesion is within the range of 0.5+/−0.1, or the image quality is inadequate to achieve such certainty, the status of the lesion may be indeterminate, although the present disclosure is not limited to any specific value.

Another aspect of the present disclosure is a computer-implemented method of distinguishing between benign and malignant skin conditions utilizing a numerical value determined from data corresponding to one or more images of skin. The method includes utilizing a computer to extract a numerical value from data corresponding to a digital image of skin, wherein the digital image corresponding to the data includes at least one region of concern comprising a potential malignancy having light regions and dark regions, and wherein the numerical value is determined, based at least in part, on an area of a selected one of the light regions or the dark regions relative to a total area, wherein the total area is equal to the sum of an area of the light regions and an area of the dark regions. The light regions and the dark regions may be determined, at least in part, utilizing a threshold value whereby portions (areas) of the image (e.g. pixels) having a brightness value above the threshold value are included in the light regions, and portions (e.g. pixels) having a brightness value below the threshold value are included in the dark regions. The threshold value may be determined for a specific set of data (image). The method further includes estimating the likelihood that the potential malignancy is malignant based, at least in part, on a comparison of the extracted numerical value to one or more predefined numerical malignancy criteria that correspond to a likelihood that the potential malignancy is malignant. The numerical value may optionally comprise an order parameter squared ($S^2$). The potential malignancy may optionally comprise a pigmented skin lesion, and the method may optionally include determining that the pigmented skin lesion is likely to be benign if the numerical value of the extracted $S^2$ is greater than or equal to a predefined benign $S^2$ value. The predefined malignant $S^2$ value may be less than the predefined benign $S^2$ value.

Another aspect of the present disclosure is a computer-implemented method of identifying margins of malignant skin lesions. The method includes utilizing a computer to create an $S^2$ spatial map from an image of skin by forming a binary image, followed by utilizing a computer to assign each pixel of the binary image a greyscale value that is equal to the average value of the adjacent pixels in the binary image, wherein the $S^2$ spatial map may be utilized to aid in determining the margins of malignant skin lesions to facilitate removal of the entire malignant lesion without removing an excessive amount of surrounding tissue that is not malignant.

In general, extracted $S^2$ values between the malignant and benign $S^2$ values may be indeterminate. Also, the predefined malignant and benign $S^2$ values may be determined by extracting a sufficiently large number of $S^2$ values from images of skin lesions that are known to be either malignant or benign. The predefined malignant and/or benign $S^2$ values may be determined, at least in part, on a required confidence level that a given lesion will be malignant or benign. For example, the predefined malignant $S^2$ values could be selected to be greater than the largest $S^2$ values of known malignant lesions to minimize or eliminate the risk that a malignant lesion is incorrectly evaluated due to an unexpectedly large $S^2$ value that is above the $S^2$ value of known malignant lesions (e.g., known malignant lesions utilized to determine the predefined malignant $S^2$ value). Similarly, the predefined benign $S^2$ value may be selected to be greater than the smallest $S^2$ values of known benign skin lesions to minimize or eliminate the risk that an indeterminate skin lesion (i.e., a lesion requiring additional evaluation to determine if it is malignant or benign) is incorrectly evaluated as benign. Furthermore, known malignant and/or benign lesions may be utilized to form a range or a series of ranges of predefined malignant and/or benign $S^2$ values corresponding to increasing confidence levels (probabilities) that a given lesion is malignant or benign. For example, $S^2$ values between 0.4-0.5 may indicate that a lesion is indeterminate, but likely not malignant, $S^2$ values between 0.3-0.4 may indicate a moderate probability that a lesion is malignant, and $S^2$ values below 0.3 may indicate a very high probability that a lesion is malignant. Similarly, $S^2$ values between 0.5-0.6 may indicate a lesion is indeterminate, but likely benign, $S^2$ values between 0.6-0.7 may indicate a moderate probability a lesion is benign, and $S^2$ values above 0.7 may indicate a very high probability that a lesion is benign. It will be understood that the numerical ranges described above are examples, and the numerical values of the predefined ranges may be different than the examples.

These and other features, advantages, and objects of the present device will be further understood and appreciated by those skilled in the art upon studying the following specification, claims, and appended drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 illustrates an $S^2$ spatial map created from an image of a skin lesion.

DETAILED DESCRIPTION

Figure 1A:
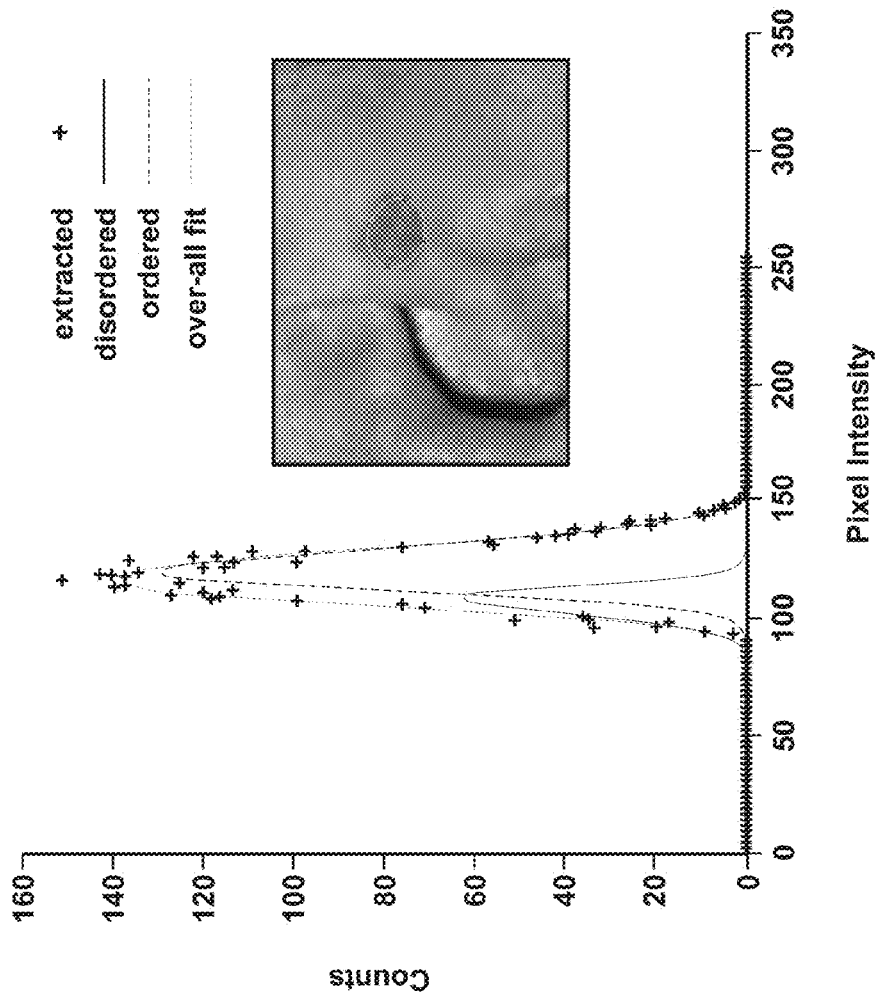
FIG. 1A is a pixel intensity histogram and image (inset) of a benign skin condition (seborrheic keratosis)

It is to be understood that the items described herein may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Additionally, unless otherwise specified, it is to be understood that discussion of a particular feature or component extending in or along a given direction or the like does not mean that the feature or component follows a straight line or axis in such a direction or that it only extends in such direction or on such a plane without other directional components or deviations, unless otherwise specified.

One aspect of the present disclosure is a method of extracting an order parameter S, or an order parameter squared ($S^2$) from images of skin lesions (FIGS. 1A-1C and 2A-2C). The extraction process is discussed in more detail below in connection with FIG. 4. As discussed in more detail below, larger $S^2$ values generally indicate that a lesion may be benign, whereas lower $S^2$ values may indicate that a skin lesion is malignant. Thus, the $S^2$ value extracted from dermatoscopic images may be utilized to determine if a skin lesion is benign or malignant. As used herein, the term "order parameter" broadly refers to S, $S^2$, or any other suitable parameter or quantity relating to a degree of order present in a physical item and/or an image of a physical item.

In general, the order parameter S specifies or quantifies the degree of disorder characterizing a specific physical sample in a number of physical systems. In some cases, it is possible to link the order parameter to a physical parameter of interest (such as band gap energy, or critical temperature). Even in cases where such a physical property is not immediately evident, comparison between samples, or quantitative analysis of physical system evolution, can be obtained by comparing order parameter values.

There are established relationships between the degree of ordering which characterizes a physical system and key system properties. Thus, an appropriate metric for ordering can, in some instances, provide the basis for a detailed understanding of the underlying mechanisms which influence properties, and suggest possible ways to control them. Quantifying system ordering is possible across multiple length scales ranging from the microscopic to the astronomical. Temporal variation of the order parameter yields valuable information regarding system evolution over a range of time scales.

It is possible to experimentally quantify the degree of disorder in physical systems using a metric such as the Bragg-Williams order parameter (S). For a perfectly ordered system S=1, for a system with complete disorder S=0, and partially ordered systems exhibit a value of S between 0 and 1. Foundational work for obtaining an experimental measurement of S was accomplished via x-ray diffraction measurements on metal binary alloys, such as CuAu and beta-brass (ZnCu). A methodology for extracting S from Raman spectra, reflection high-energy electron diffraction (RHEED), and electron microscopy images has also been developed. These techniques have been applied to heterovalent ternary semiconductors to establish a relationship between disorder and critical system-level properties of the material, specifically the band gap. However, the approach applies to semiconductors in general, including silicon and graphene, and also organic-based polymers as well as biological systems in the context of, for example, viruses and vaccines and skin conditions.

For the case of an atomic lattice with two elements (A and B) the Bragg-Williams order parameter is defined as $S=r_A+r_B-1$, where $r_A$ ($r_B$) is the ratio of A (B) atoms on A (B) lattice sites; in the case of N different elements $S=(r_A+r_B+\ldots+r_N-1)/(N-1)$. However, experimental techniques do not require knowledge apriori of the definition of S, i.e., a methodology for extracting S from experimental techniques, whether x-ray diffraction, RHEED, Raman spectroscopy, or electron microscopy, applies regardless of the number of elements responsible for the disorder. While the full range of S is from 0 to 1, the maximum value achievable in a given system is limited by the compositional stoichiometry, i.e., the perfectly ordered state S=1 is only achievable when there are equal amounts of all constituent elements. For the specific case of two elements, where the composition x is defined as $$x = \frac{N_A}{N_A + N_B}$$

with $N_A$ ($N_B$) equal to the number of A (B) elements in the system, the maximum S value is $S_{max}=2x$ for $x<0.5$ and $2(1-x)$ for $x>0.5$; similar constraints can be derived for cases with a higher number of unique elements. Additionally, system-level properties dominated by pair interactions have a linear relationship with $S^2$. By using a spin modeling technique (each element type is assigned a different spin), in conjunction with cluster expansion theory limited to single and pair-wise interaction terms, it can be shown that $P(x, S)=S^2[P(x=0.5, S=1)-P(x, 0)]-P(x, 0)$. For this reason, and the fact that $S^2$ is the value often obtained through experimental measurement, the squared order parameter $S^2$ is discussed herein instead of S.

Figure 1B:
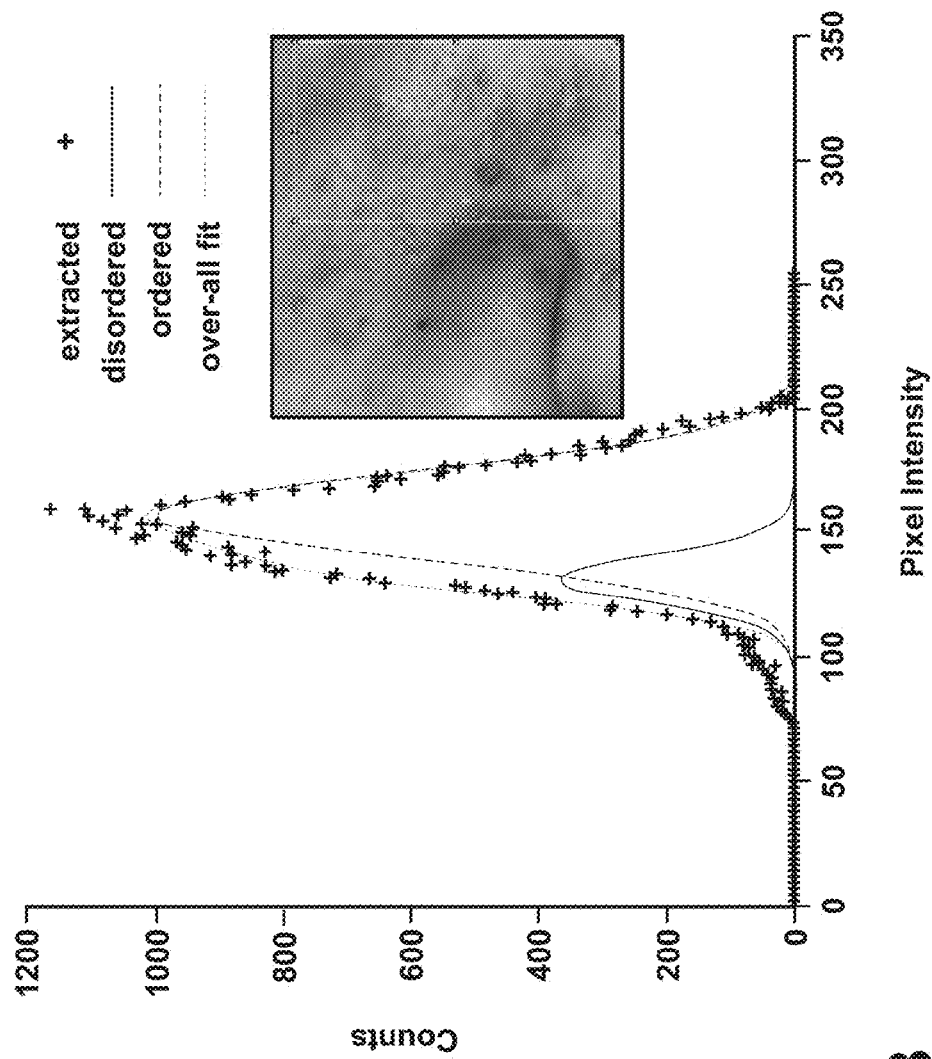
FIG. 1B is a pixel intensity histogram and image (inset) of a benign skin condition (actinic keratosis)
Figure 1C:
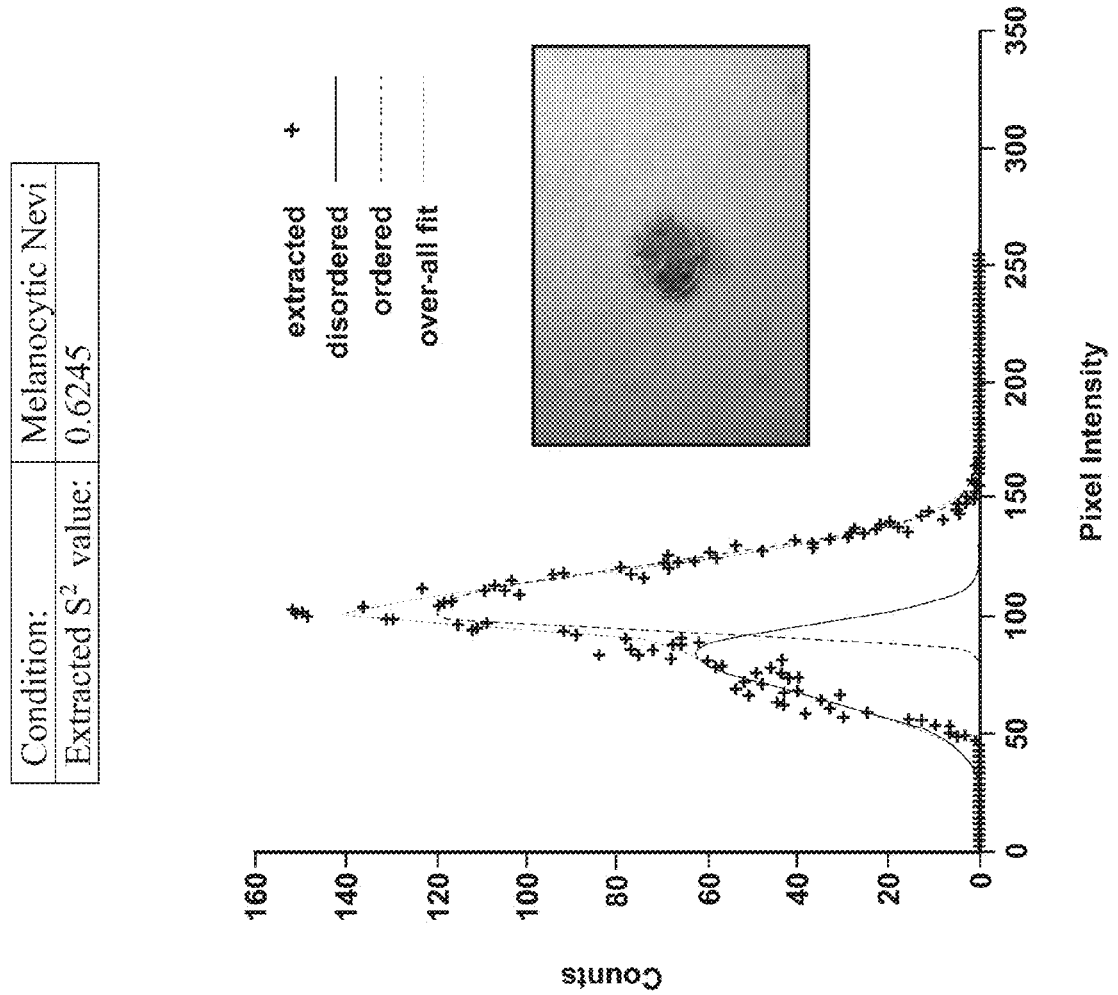
FIG. 1C is a pixel intensity histogram and image (inset) of a benign skin condition (melanocytic nevi)

FIGS. 1A-1C are pixel intensity histograms (graphs) for benign skin lesions showing disorder-contribution curve fits, order-contribution curve fits, and over-all fits based on a region of interest of a digital dermatoscopic image inset in each graph. As discussed in more detail below, the $S^2$ value for a lesion is extracted from the region of interest. As discussed in more detail below in connection with FIG. 4, the region of interest may be selected by a user, a computer-implemented algorithm, or a combination thereof. The image (inset) of FIG. 1 shows seborrheic keratosis, and a region of interest that is bounded by the yellow ellipse around the pigmented region of the skin.

The inset of FIG. 1B is a dermatoscopic image of actinic keratosis. As is shown in the inset, the region of interest in this example is rectangular.

The inset of FIG. 1C is a dermatoscopic image of melanocytic nevi, and the region of interest comprises an ellipse that is approximately circular.

Figure 2A:
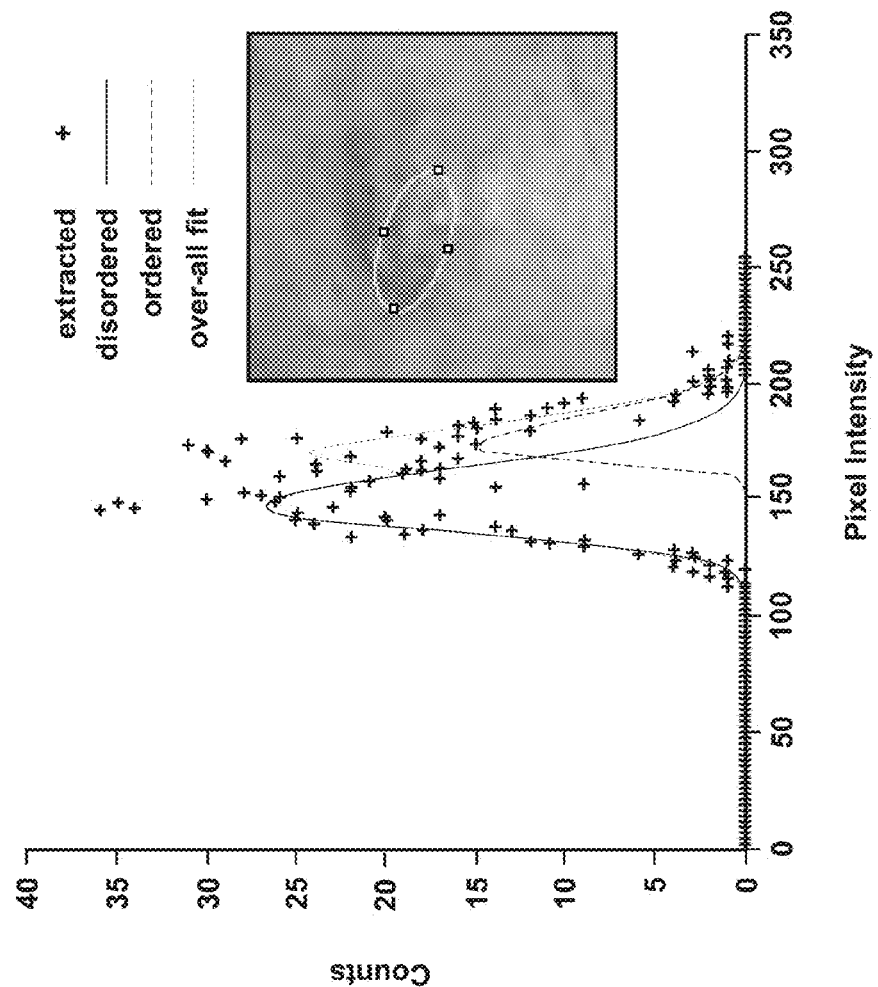
FIG. 2A is a pixel intensity histogram and image (inset) of a malignant skin condition (basal cell carcinoma)
Figure 2B:
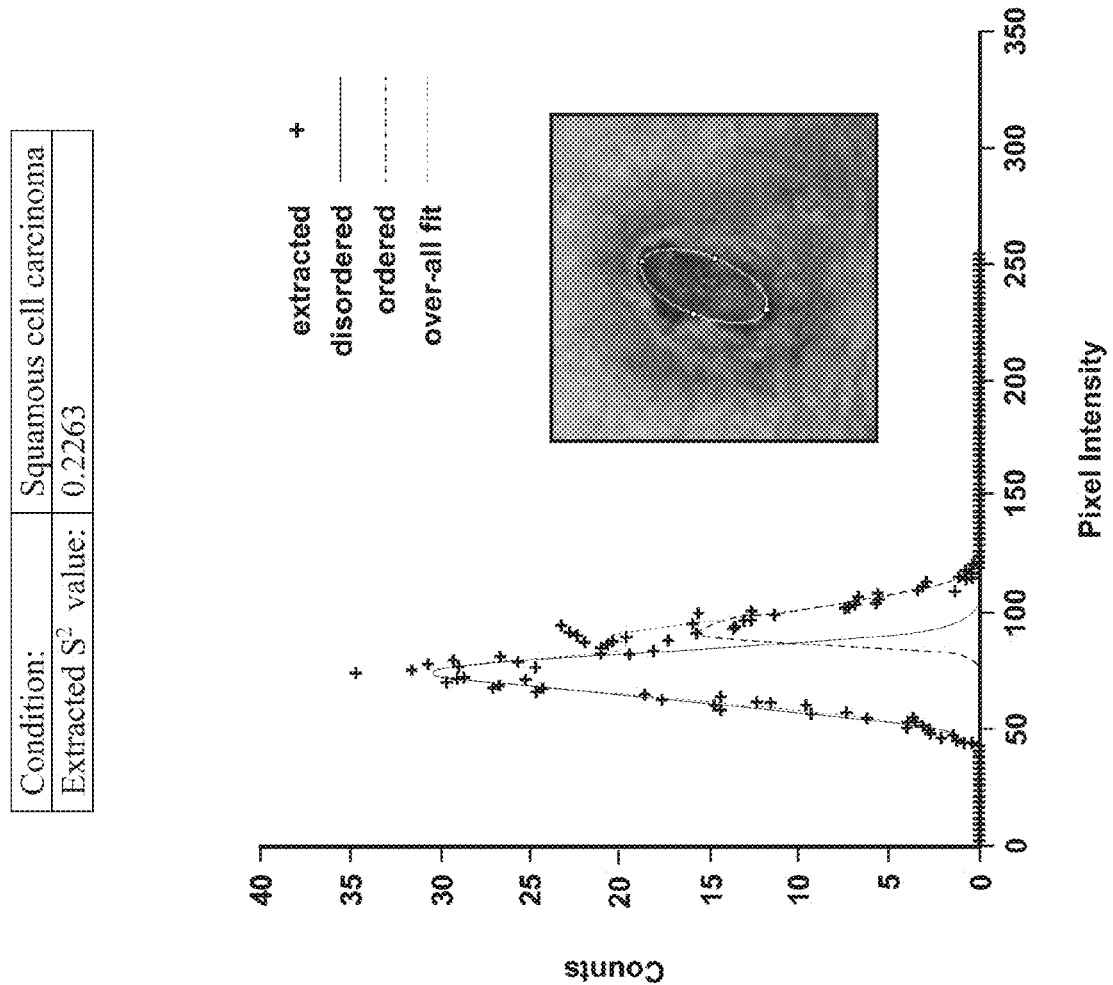
FIG. 2B is a pixel intensity histogram and image (inset) of a malignant skin condition (squamous cell carcinoma)
Figure 2C:
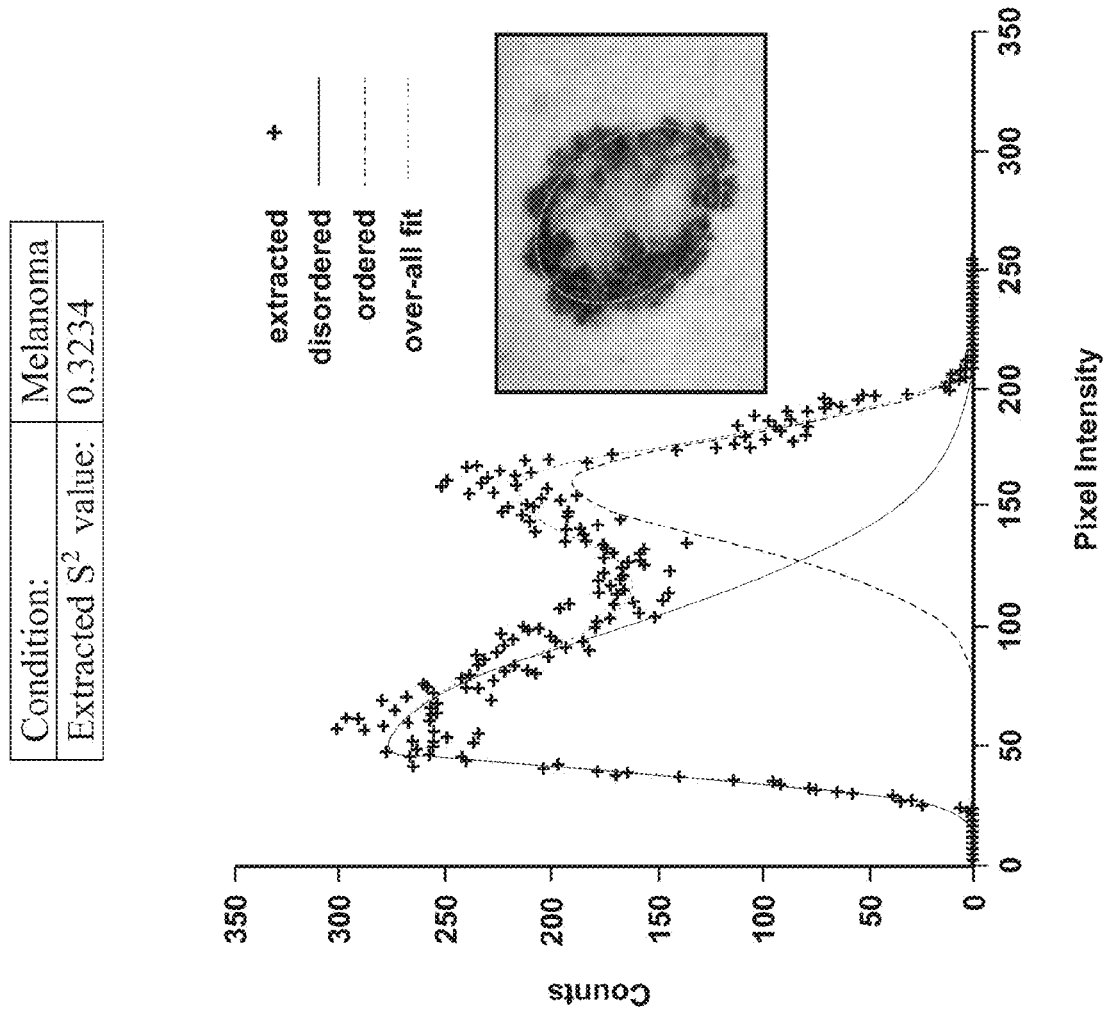
FIG. 2C is a pixel intensity histogram and image (inset) of a malignant skin condition (melanoma)

FIGS. 2A-2C are pixel intensity (brightness) histograms and insets of corresponding digital dermatoscopic images of malignant skin lesions. It will be understood that a pixel having very low intensity will be darker black in greyscale, and a pixel having high intensity will be very light (white) in greyscale. Specifically, the inset for FIG. 2A is a dermatoscopic image of a basal cell carcinoma, the inset of FIG. 2B is a dermatoscopic image of a squamous cell carcinoma, and the inset of FIG. 2C is a dermatoscopic image of melanoma.

In general, the region of interest is selected to surround (include) the pigmented region, and to exclude all or most of the adjacent skin that is not pigmented. Thus, the region of interest typically includes a large portion of the pigmented lesion, without including adjacent skin that is not pigmented. The region of interest may be selected by an individual evaluating an image, or by a computer that is configured (e.g. programmed) to determine a boundary around an area of interest.

The extracted $S^2$ values for the benign skin conditions of FIGS. 1A-1C are 0.7218, 0.7160, and 0.6245, respectively. The extracted $S^2$ values for the malignant skin conditions for FIGS. 2A-2C are 0.2766, 0.2263, and 0.3234, respectively. Thus, in the examples of FIGS. 1A-2C and FIGS. 2A-2C, the $S^2$ values of the benign skin conditions are significantly greater than 0.5, and the extracted $S^2$ values for malignant skin conditions are significantly less than 0.5.

Figure 3:
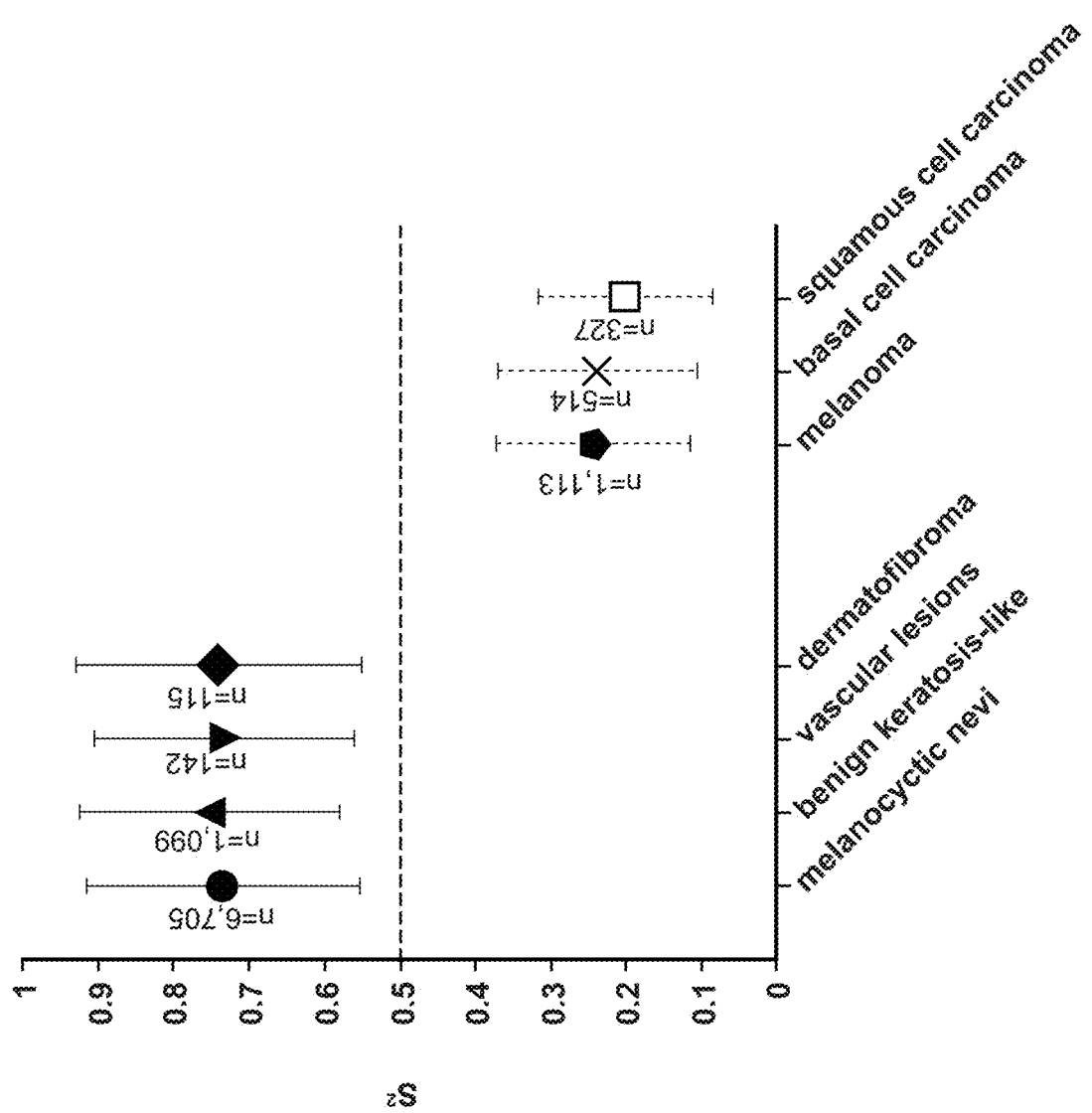
FIG. 3 is a plot of order parameter squared ($S^2$) value for four separate benign types of skin lesions and three separate malignant types of skin lesions.

The methodology was applied to all images of skin lesions in the HAM10000 dataset, the results of which are shown in FIG. 3. FIG. 3 comprises a plot of extracted $S^2$ values for four separate benign skin lesions, and three separate malignant types of skin lesions. The number n adjacent to each line is the number of different samples evaluated for that condition. The symbol denotes the average value over n samples, and the bars denote the first standard deviation from the average value. The results shown in FIG. 3 indicate a significant separation in $S^2$ values between the benign skin lesions (green points) and malignant skin lesions (red points), with all malignant lesions having an $S^2$ value below 0.5 and all benign lesions having an $S^2$ value greater than 0.5.

As discussed above, S=1 corresponds to a perfectly ordered system, and a completely disordered system corresponds to S=0. Not wishing to be bound by any specific theory, it is hypothesized that it is the order parameter associated with discrete skin cells that are actually measured when $S^2$ is extracted from images of skin lesions, leading to the results described herein.

Figure 4:
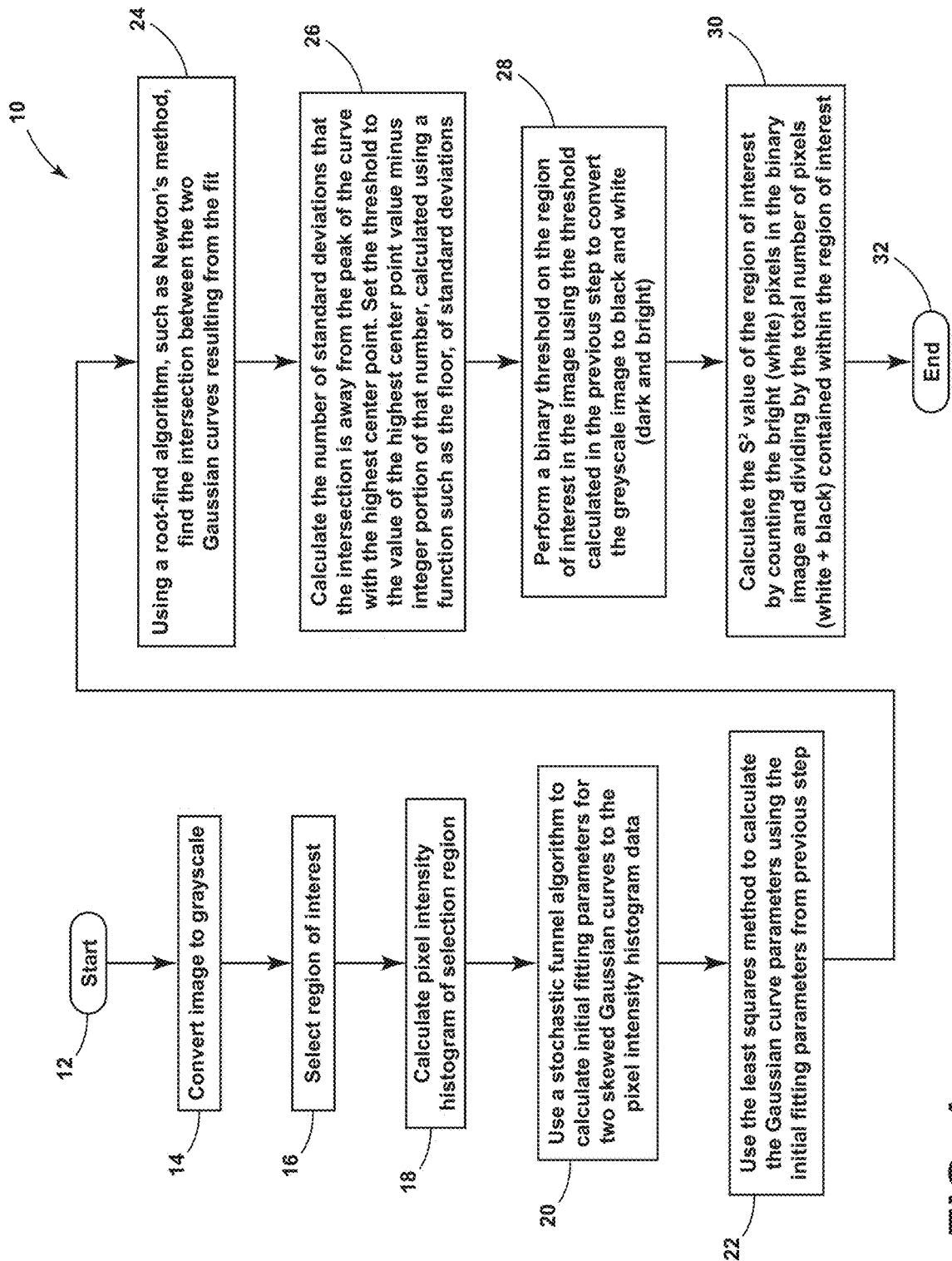
FIG. 4 is a flowchart showing a method of extracting order parameter squared ($S^2$) from an image.

With reference to FIG. 4, a process 10 for calculating the threshold value of an image 10 is shown. One or more steps of process 10 may be implemented utilizing a computer. For example, a computer may be configured (programmed) to execute one or more of the steps of process 10. Process 10 starts as shown at 12, and step 14 includes converting the image to greyscale. A region of interest may be selected as shown in step 16. In general, the region of interest may be selected before or after converting an image to greyscale. The region of interest may be selected by an individual inspecting one or more dermatoscopic images, or the region of interest may be selected by a computer algorithm. As shown in FIGS. 1A-1C and FIGS. 2A-2C, the region of interest may have virtually any shape as required to bound a representative portion (region) of the skin lesion.

The process 10 further includes calculating a pixel intensity histogram of the selected region (see, e.g., FIGS. 1A-1C and 2A-2C). At step 20, an algorithm (e.g., a stochastic funnel algorithm) is used to calculate initial fitting parameters for two skewed Gaussian curves to the pixel intensity (brightness) histogram data. In the examples of FIGS. 1A-1C and 2A-2C, the skewed Gaussian curves are shown as the disordered and ordered curves, and the over-all fit is also shown. Referring again to FIG. 4, at step 22, the least squares method may be used to calculate the Gaussian curve parameters using the initial fitting parameters from step 20.

At step 24, a root-finding algorithm (e.g., Newton's method) is used to find the intersection between the two Gaussian curves resulting from the curve fit. At step 26, a number of standard deviations that the intersection is away from the curve where the highest center point is calculated. A threshold value is set to the value of the highest center point value minus the floor of that number of standard deviations. As discussed below, the threshold value may be used to determine which pixels are "bright" (white), and which pixels are "dark" (black).

At step 28, a binary threshold is performed on the region of interest in the image using the threshold calculated in step 26. Pixels having an intensity that is greater than the threshold value are given (assigned) a white (high) intensity value, and pixels having an intensity that is less than the threshold value are given (assigned) a black (low) intensity value. In general, the result of the binary threshold is a black (dark) and white (bright) image (not shown) having white (ordered) regions and black (disordered) regions. At step 30, a numerical value, which may comprise the squared order parameter ($S^2$) value of the region of interest, is calculated by counting the bright (white) pixels in the thresholded image and dividing this number by the total number of pixels contained with the region of interest. The total number of pixels is equal to the sum of the number of dark (black) pixels and the number of bright (white) pixels. Because the sizes (areas) of each of the pixels are the same, the $S^2$ value is the ratio of the area of the bright regions to the total area. The method 10 then ends as shown at 32. It will be understood that the numerical value may also comprise the ratio of the area of the dark regions to the total area (i.e. $1-S^2$).

The numerical value (e.g. $S^2$) determined utilizing the process 10 of FIG. 4 may then be compared to predefined criteria (e.g. $S^2$) values extracted from images known to be malignant or benign in order to estimate the chances that the region of interest includes a malignant skin condition. For example, a computer may be configured (programmed) to generate a "likely benign" output or signal if the numerical value of $S^2$ is greater than a predefined value (e.g. 0.4, 0.5, 0.6), and a computer may be configured (programmed) to generate a "likely malignant" output or signal if the numerical value of $S^2$ is less than the predefined value (e.g. 0.4, 0.5, 0.6). Also, a computer may be configured to generate an "indeterminate signal" is the numerical value of $S^2$ is between a predefined "likely benign" numerical value (e.g. 0.55) and a predefined "likely malignant" numerical value (e.g. 0.4).

Figure 5:
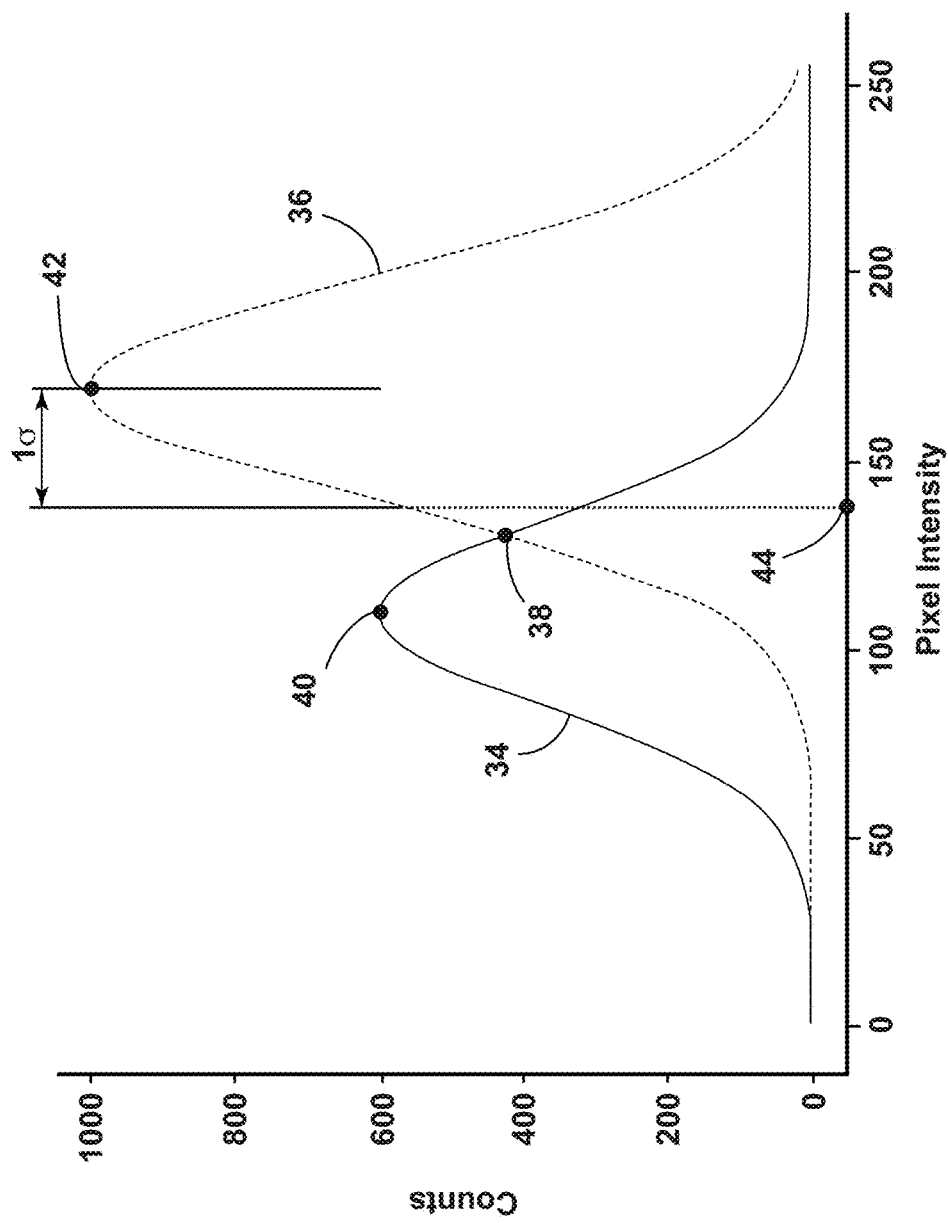
FIG. 5 is a graph showing an aspect of the process of FIG. 4.

FIG. 5 shows the process for finding the threshold value 44 from the fitted curves 35 and 36. As discussed above in connection with FIG. 4, a disordered curve 34 and ordered curve 36 may be fitted using, for example, skewed Gaussian curved parameters. The inner section 38 of the curves 34 and 36 may then be determined (e.g., using Newton's method), and the threshold value 44 may then be determined. In the example of FIG. 5, the disordered curve 34 has a center point (peak) 40, and the ordered curve 36 has a center point (peak) 42. In the example of FIG. 5, the threshold value 44 is approximately 140. It will be understood that the present disclosure is not limited to a specific technique or approach for determining the threshold value.

With further reference to FIG. 6, an $S^2$ (or S) spatial map 50 (greyscale) may be derived or extracted from an original image 10A. In general, a single (global average) $S^2$ value can be extracted from an image, or it can be restricted to a smaller region and values can be extracted that are specific to those regions. If $S^2$ images are extracted at different points in time, the $S^2$ spatial maps can be compared to see not only changes over time, but more details (e.g., where it is changing). Also, spatial mapping of $S^2$ for an image of a lesion facilitates determining the margins of malignant lesions, which may be required for surgically removing the lesions.

The greyscale $S^2$ spatial map 50 may be created by first determining the $S^2$ value of the entire original image 10A. Then, a binary image (black and white) is created from the threshold process (e.g. step 26, FIG. 4) of the $S^2$ analysis to generate the $S^2$ grey map 50. A box blur or normalization operation is applied to the binary image, which results in each pixel in the resulting image having a value equal to the average value (greyscale) of its neighboring pixels in the input binary image. For example, a black pixel may have a value of 0, and a white pixel may have a value of 255, and a greyscale number may have a value between 0 and 255 as shown by a greyscale 52. Thus, in this example, the value that results from the taking the average value of the neighboring pixels in the binary image, which are all white (255) or black (0), is a greyscale value between 0 and 255. The resulting image from this process is the $S^2$ map 50. The number of neighboring pixels included in the normalization process may be varied based on the desired resolution of the $S^2$ map 50 and the overall resolution of the original image.

It will be understood that the processes described herein comprise a screening tool that may assist in determining if an image includes benign or malignant skin conditions. However, the processes described herein are not intended to be the sole criteria for determining if a skin condition is malignant, which determination will require additional evaluation and testing by medical specialists.

The examples described above generally relate to skin lesions. However, the process described above may also be utilized to evaluate other malignancies, including other types of tumors besides skin lesions. In general, virtually any image of a potential malignancy may be evaluated according to the process described in connection with FIGS. 4 and 5. It will be understood that the images could comprise virtually any type of image.

It will be understood by one having ordinary skill in the art that construction of the described device and other components is not limited to any specific material. Other exemplary embodiments of the device disclosed herein may be formed from a wide variety of materials, unless described otherwise herein.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

The above description is considered that of the illustrated embodiments only. Modifications of the processes will occur to those skilled in the art and to those who make or use the processes. Therefore, it is understood that the embodiments shown in the drawings and described above are merely for illustrative purposes and not intended to limit the scope of the disclosure, which is defined by the following claims as interpreted according to the principles of patent law, including the Doctrine of Equivalents.

What is claimed is:

1. A computer-implemented method of distinguishing between benign and malignant skin conditions utilizing an order parameter, the method comprising:
   utilizing a computer to extract a numerical value corresponding to an order parameter squared ($S^2$) from image data corresponding to an image of skin, wherein the image data includes at least one pigmented skin lesion having light regions and dark regions, and wherein $S^2$ comprises a numerical value quantifying a degree of order present in the image data, and wherein the extracted numerical value comprises a ratio of an area of the light regions to a total area that is equal to the sum of an area of the light regions and an area of the dark regions;

comparing the extracted numerical value to a predefined malignant value; and determining that the pigmented skin lesion is likely to be malignant if the numerical value of the extracted $S^2$ is less than or equal to the predefined malignant $S^2$ value.

2. The method of claim 1, wherein:
the extracted numerical value comprises an extracted $S^2$ value; and including:
determining that the pigmented skin lesion is likely to be benign if the extracted $S^2$ value is greater than or equal to a predefined benign $S^2$ value.

3. The method of claim 2, wherein:
the predefined malignant $S^2$ value is less than the predefined benign $S^2$ value.

4. The method of claim 3, including:
determining that the malignancy of the pigmented skin lesion is indeterminate if the extracted $S^2$ value is between the predefined malignant $S^2$ value and the predefined benign $S^2$ value.

5. The method of claim 2, wherein:
the predefined malignant $S^2$ value is equal to the predefined benign $S^2$ value.

6. The method of claim 1, wherein:
the predefined malignant value comprises a predefined malignant $S^2$ value that is determined by utilizing a computer to extract a numerical value of $S^2$ from a plurality of sets of data corresponding to images of skin including malignant pigmented skin lesions.

7. The method of claim 6, wherein:
the predefined malignant $S^2$ value is equal to or greater than a largest numerical value of $S^2$ extracted from the corresponding to images of skin including malignant pigmented skin lesions.

8. The method of claim 1, wherein:
extracting a numerical value corresponding to $S^2$ from image data includes selecting a region of interest that includes at least a portion of the at least one pigmented skin lesion.

9. The method of claim 8, wherein:
the image data includes at least some skin that is free of skin lesions; and
the region of interest does not include skin that is free of skin lesions.

10. The method of claim 8, wherein:
the image data comprises a plurality of pixels;
extracting a numerical value corresponding to $S^2$ from the image data includes utilizing a computer to create a pixel intensity histogram of the region of interest.

11. The method of claim 10, wherein:
extracting a numerical value corresponding to $S^2$ from the image data includes utilizing a computer to fit first and second curves to the pixel intensity histogram corresponding to the light and dark regions, respectively.

12. The method of claim 11, wherein:
extracting a numerical value corresponding to $S^2$ from image data includes utilizing a computer to convert the image data to greyscale image data;
utilizing a computer to determine a threshold value of the pixel intensity between peaks of the first and second curves; and utilizing a computer to perform a binary threshold on the region of interest using the threshold value to form a set of digital data corresponding to an image having only black and white pixels.

13. The method of claim 8, wherein:
the region of interest is selected by creating a curved border around the region of interest.

14. The method of claim 1, including:
utilizing a plurality of non-equal predefined malignant values corresponding to increasing probability that a skin lesion is malignant to determine a risk that a specific skin lesion is malignant.

15. The method of claim 1, wherein:
the image data comprises a selected one of digital optical image data or image data from a microscope.

16. The method of claim 1, wherein:
the skin lesion or region of skin of interest is measured using Raman spectroscopy.

17. The method of claim 8, wherein:
selecting a region of interest comprises utilizing a computer to determine a border using an algorithm.

18. The method of claim 17, wherein:
the algorithm comprises a morphological filter operation.

19. A method of identifying margins of malignant skin lesions, the method comprising: utilizing a computer to create an order parameter squared S.sup.2 spatial map from image data corresponding to an image of skin by forming binary image data corresponding to a binary image; followed by utilizing a computer to assign each pixel of the binary image data a greyscale value that is equal to the average value of the adjacent pixels in the binary image data; and wherein the S.sup.2 spatial map is configured to be utilized to aid in determining the margins of malignant skin lesions to facilitate removal of the entire malignant lesion without removing an excessive amount of surrounding tissue that is not malignant.

20. A computer-implemented method of distinguishing between benign and malignant skin conditions utilizing a numerical value determined from data corresponding to one or more images of skin, the method comprising: utilizing a computer to extract a numerical value from image data corresponding to a digital image of skin, wherein the digital image corresponding to the image data includes at least one region of concern comprising a potential malignancy having a total area including light regions and dark regions, and wherein the numerical value is determined, based at least in part, on an area of a selected one of the light regions and the dark regions to a total area, wherein the total area is equal to the sum of the areas of the light regions and the areas of the dark regions; estimating the likelihood that the potential malignancy is malignant based, at least in part, on a comparison of the extracted numerical value to one or more predefined numerical malignancy criteria that take into account the likelihood that the potential malignancy is malignant, wherein the extracted numerical value comprises an extracted numerical value of an order parameter squared ($S^2$).

21. The method of claim 20, wherein:
the numerical value is determined by dividing the area of the light regions by the total area.

22. The method of claim 21, including:
determining a threshold brightness value for the digital image;
determining the area of the light regions by summing the areas of the pixels having a brightness value above the threshold brightness value.

23. The method of claim 21, wherein: the potential malignancy comprises a pigmented skin lesion; and including: determining that the pigmented skin lesion is likely to be benign if the extracted numerical value of $S^2$ is greater than or equal to a predefined benign $S^2$ value.

24. The method of claim 23, wherein:
the predefined malignant $S^2$ value is less than the predefined benign $S^2$ value.

25. The method of claim 24, including:
determining that the malignancy of the pigmented skin lesion is indeterminate if the extracted numerical value of $S^2$ is between the predefined malignant $S^2$ value and the predefined benign $S^2$ value.

\* \* \* \* \*